United States Patent [19]

Johnson et al.

[11] Patent Number: 4,868,181
[45] Date of Patent: Sep. 19, 1989

[54] 1,4-DIHYDROPYRIDINE DERIVATIVES WITH CALCIUM AGONIST AND ALPHA₁-ANTAGONIST ACTIVITY

[75] Inventors: Alexander L. Johnson, Wilmington, Del.; Philip Ma, Chadds Ford; Petrus B. M. W. M. Timmermans, Kennett Square, both of Pa.; Ruth R. Wexler, Wilmington, Del.

[73] Assignee: E. I. Du Pont de Nemours and Company, Wilmington, Del.

[21] Appl. No.: 64,361

[22] Filed: Jun. 30, 1987

Related U.S. Application Data

[63] Continuation-in-part of Ser. No. 892,293, Aug. 4, 1986, abandoned.

[51] Int. Cl.⁴ .................. A61K 31/395; A61K 31/44; A61K 31/435; A61K 31/495; A61K 31/505; C07D 401/02; C07D 401/12; C07D 401/14

[52] U.S. Cl. .................... 514/252; 514/210; 514/218; 514/253; 514/258; 514/275; 514/291; 514/301; 514/302; 514/334; 514/341; 540/481; 540/597; 540/598; 540/599; 540/600; 540/601; 544/284; 544/295; 544/360; 544/370; 546/89; 546/114; 546/115; 546/289; 546/255; 546/256; 546/257; 546/262; 546/263; 546/264; 546/266; 546/267; 546/286; 546/287; 546/289; 548/95

[58] Field of Search ........... 540/575, 481, 597, 598, 540/599, 600, 601; 544/284, 295, 360, 370; 546/89, 286, 287, 289, 114, 115, 255, 256, 257, 262, 263, 264, 266, 267; 548/95; 514/210, 302, 218, 334, 252, 253, 341, 258, 275, 291, 301

[56] References Cited

U.S. PATENT DOCUMENTS

| | | | |
|---|---|---|---|
| 3,985,758 | 10/1976 | Murakami et al. | 260/295.5 R |
| 4,248,873 | 2/1981 | Bossert et al. | 424/256 |
| 4,256,749 | 3/1981 | Horstmann et al. | 424/251 |
| 4,448,964 | 5/1984 | Muto et al. | 546/194 |
| 4,532,248 | 7/1985 | Franckowiak et al. | 514/302 |
| 4,537,881 | 8/1985 | Heiker et al. | 514/25 |

FOREIGN PATENT DOCUMENTS

| | | |
|---|---|---|
| 6483786 | 5/1986 | Australia . |
| 5897886 | 6/1986 | Australia . |
| 0097821 | 1/1984 | European Pat. Off. . |
| 0138505 | 4/1985 | European Pat. Off. . |
| 0151006 | 6/1985 | European Pat. Off. . |
| 0205511 | 7/1986 | European Pat. Off. . |
| 0194047 | 9/1986 | European Pat. Off. . |
| 3512995 | 6/1983 | Fed. Rep. of Germany . |
| 3339861 | 5/1985 | Fed. Rep. of Germany . |
| 3600596 | 7/1987 | Fed. Rep. of Germany . |
| 3601397 | 7/1987 | Fed. Rep. of Germany . |
| 2149659 | 3/1987 | Japan . |
| 866957 | 12/1986 | South Africa . |
| 2158065 | 11/1985 | United Kingdom . |

OTHER PUBLICATIONS

Nature, vol. 303, 9 Jun. 1983, pp. 535-537.
Biochemical and Biophysical Research Communications, vol. 118, No. 3, Feb. 14, 1984, pp. 842-847.
Arzneim-Forsch Drug Research, vol. 33 (11), Nr 9, 1983, pp. 1268-1272.
E. Schroder et al., "Pharmazeutische Chemie", 1982, pp. 677, 678, Publisher George Thieme, Stuttgart.
Progress in Pharmacology, vol. 5/1, 1982, pp. 25-52, Stuttgart; R. Mannhold et al.: "Qualitative and Quantitative Structure-Activity Relationships of Specific Ca Antagonists", FIG. 10, p. 44.
Chemical & Pharmaceutical Bulletin, vol. 33, No. 9, Sep. 1985, pp. 3787-3797, Tokyo, JP; K. Meguro et al.: "New 1,4-dihydropyridine Derivatives with Potent and Long-Lasting Hypotensive Effect", Example 33, p. 3791.

*Primary Examiner*—Cecilia Shen
*Attorney, Agent, or Firm*—Robert W. Black; Gildo E. Fato

[57] ABSTRACT 1,4-Dihydropyridine derivatives which combine both calcium agonist and alpha₁-antagonist activity are useful in treating congestive heart failure. These derivatives are compounds having the formula:

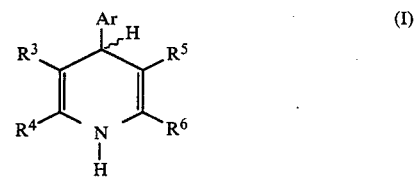

(I)

wherein Ar, $R^3$, $R^4$, $R^5$ and $R^6$ are defined in the specification.

72 Claims, No Drawings

1,4-DIHYDROPYRIDINE DERIVATIVES WITH CALCIUM AGONIST AND ALPHA₁-ANTAGONIST ACTIVITY

RELATED APPLICATION

This application is a continuation-in-part of copending U.S. application Ser. No. 892,293 filed Aug. 4, 1986, now abandoned.

FIELD OF THE INVENTION

This invention relates to certain novel 1,4-dihydropyridines, processes for their preparation, pharmaceutical compositions containing them, and methods of using them to treat congestive heart failure, and more particularly to such 1,4-dihydropyridines having both calcium agonist and alpha₁-antagonist activity and which combine both calcium agonist and alpha₁-antagonist activity and are useful in the treatment of congestive heart failure.

BACKGROUND OF THE INVENTION

Over the past decade, dihydropyridine calcium antagonists have become widely known therapeutic agents having vasodilator properties which can be used as antihypertensives and coronary agents. More recently, it has been found that small structural modifications produce dihydropyridines with effects diametrically opposed to those of calcium antagonists. In contrast to the calcium antagonists, dihydropyridines such as Bay K8644 and CGP28392 promote an influx of calcium ions, therefore producing positive inotropic and vasoconstrictor effects. Bay K8644 is more than 10 times as potent as a calcium agonist than CGP28392. However, Bay K8644 is toxic because it causes coronary vasoconstriction and therefore it is only useful as a therapeutic tool to ascertain the function of calcium entry blockers but is not useful in therapeutics as a cardiotonic.

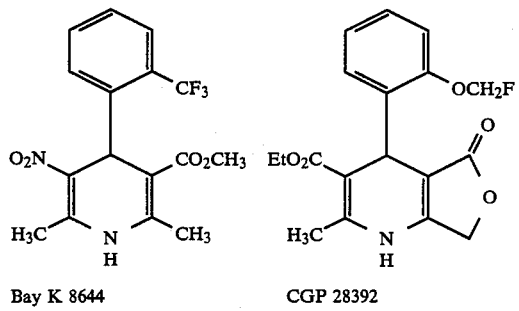

Bay K 8644    CGP 28392

Representative of the art in the field of dihydropyridine calcium agonists are U.S. Pat. No. 4,248,873 issued Febr. 3, 1981, published European Patent Application No. 0071819, U.S. Pat. Nos. 4,537,881 issued Aug. 27, 1985 and 4,532,248 issued July 30, 1985 amongst others. Literature references include M. Schram, et al., *Nature,* 303, 535 (1983); M. Schram et al., *Arzneim-Forsch.,* 33, 1268 (1983); P. Erne et al., *Biochem. Biophys. Res. Commun.,* 118, 842 (1984).

Combining calcium agonist properties and alpha₁-adrenergic blocking properties in a single molecular structure provides a new and attractive principle for the treatment of congestive heart failure. The combination of these two principles provides a novel class of cardiotonics which have minor cardiac stimulatory effects in combination with pronounced vasodilator properties. The detrimental vasoconstricting properties which are normally associated with dihydropyridine calcium agonists are minimized by including the alpha₁-adrenergic blocking properties which cause dilation of the peripheral vasculature.

SUMMARY OF THE INVENTION

According to the present invention there is provided to new 1,4-dihydropyridine derivatives of the general Formula (I) which possess both calcium channel activity and alpha₁-adrenergic blocking properties and are useful in the treatment of congestive heart failure. These compounds have the formula:

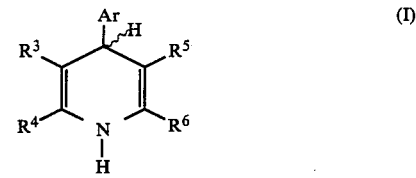

or a pharmaceutically acceptable salt thereof wherein Ar is

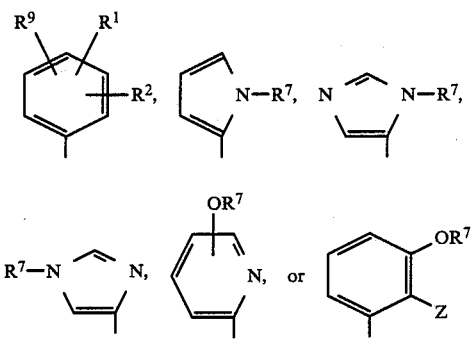

where
Z and $R^5$ are taken together as as

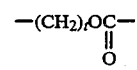

where t is 0 to 6;
$R^1$ and $R^2$ independently are H, alkyl of 1-4 carbon atoms, haloalkyl of 1-4 carbon atoms, haloalkoxy of 1-4 carbon atoms, alkoxy of 1-10 carbon atoms, halogen, $NO_2$, $(CH_2)_qXR^7$, $XCH_2(C_2-C_9$ alkenyl)$R^7$, or $XCH_2(C_2-C_9$ alkynyl)$R^7$; provided that both $R^1$ and $R^2$ are not hydrogen except when $R^5$ is $CO_2R^7$ or $COR^7$;
$R^3$ independently is $NO_2$, H, CN, or $CONH_2$, or taken together with $R^4$ is

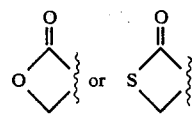

$R^4$ and $R^6$ independently are alkyl of 1-4 carbon atoms, CN, $CH_2OH$, or $CH_2OCH_2CH_2NH_2$;

$R^5$ independently is $CO_2R^7$ or $COR^7$ when $R^1$ and $R^2$ are other than $(CH_2)_qXR^7$, $XCH_2(C_2-C_9,\text{-alkenyl})R^7$, or $XCH_2(C_2-C_9 \text{ alkynyl})R^7$, and can also be an alkyl ester of 1–10 carbon atoms,

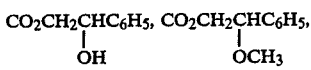

$NO_2$, or phenyl NHCO when one of $R^1$ or $R^2$ is $(CH_2)_qXR^7$, $XCH_2$ alkenyl)$R^7$, or $XCH_2(C_2-C_9$ alkynyl)$R^7$, or is taken together with Z as

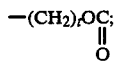

$R^7$ is selected from $-(A)_r-NH-Y-Ar'$, or

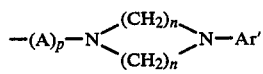

where
A is a straight or branched alkyl, alkenyl or alkynyl chain
Ar' is phenyl with one or two substituents selected from alkyl of 1–4 carbon atoms, haloalkyl of 1–4 carbon atoms, alkoxy of 1–4 carbon atoms, halogen, and $NO_2$; 2-, 3- or 4-pyridine; 2,6-pyrimidine;

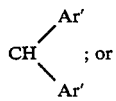

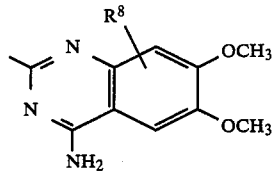

$R^8$ is H or $OCH_3$;
$R^9$ is H, halogen, $NO_2$, alkoxy of 1–4 carbon atoms, or alkyl of 1–4 carbon atoms;
X is O, S or NH;
Y is $(CH_2)_q$, $(CH_2)_nO$, $(CH_2)_nNH$ or $(CH_2)_nS$;
n is independently 1, 2 or 3;
p is 0 to 10;
q is 0, 1 or 2 and;
r is 1 to 10 provided that:
(1) when $R^5$ is $CO_2R^7$ and $R^7$ is

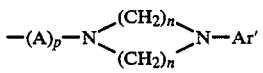

or where $R^2$ is $(CH_2)_qXR^7$, then p cannot be 0; and
(2) when $R^5$ is $COR^7$, then $R^7$ must be

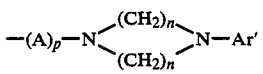

and p must be 0.

The compounds of the present invention can exist as optical isomers and both the racemic mixtures of these isomers as well as the individual optical isomer which confers agonist activity are within the scope of the present invention. The racemic mixtures can be separated into their individual isomers by well known techniques such as the separation of the diastereomeric salts formed with optically active acids, followed by conversion back to the optically active 1,4-dihydropyridine.

Also provided are pharmaceutical compositions comprising a suitable pharmaceutical carrier and a compound of Formula (I) and methods of using the compounds of Formula (I) to treat congestive heart failure.

Further provided are processes for preparing compounds of Formula (I), which processes will be described in detail hereinafter.

PREFERRED EMBODIMENTS

Preferred compounds are those of Formula (I) wherein:
(a) Ar is

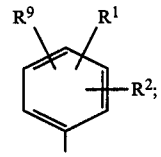

or
(b) One of $R^1$ and $R^2$ is hydrogen and the other is Cl, $CF_3$, $NO_2$, $OCH_3$ or $OR^7$, and $R^9$ is H or halogen; or
(c) $R^3$ independently is $NO_2$, or taken together with $R^4$ is

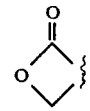

or
(d) $R^4$ and $R^6$ independently are alkyl of 1–4 carbon atoms, $CH_2OCH_2CH_2NH_2$; or
(e)
  (i) $R^5$ is $CO_2R^7$ or $COR^7$ when $R^1$ and $R^2$ are other than $(CH_2)_qXR^7$, $XCH_2(C_2-C_9$ alkenyl)$R^7$ or $XCH_2(C_2-C_9$ alkynyl)$R^7$;
  (ii) $R^5$ is an alkyl ester of 1–10, carbon atoms, $NO_2$, or phenyl NHCO when one of $R^1$ or $R^2$ is $OR^7$; or
(f)
$R^7$ is $-(CH_2)_r-NH-(CH_2)_n-O-Ar'$, or

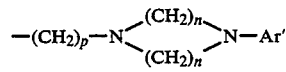

where
Ar' is

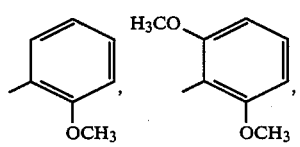

[Structure: quinazoline-like with NH2, N, OCH3, OCH3, and methyl-N]

2-pyridine, or 2,6-pyrimidine and (g) $R^9$ is H or halogen; and
n, p, $R^4$, $R^6$ and $R^8$ are as defined previously.

Most preferred are preferred compounds where:

(a) one of $R^1$ and $R^2$ is $OR^7$ with the proviso that $R^5$=alkylester of 1–10 carbon atoms;
(b) $R^3$ is $NO_2$; or
(c) $R^4=R^6$ is alkyl of 1–4 carbons, preferably $CH_3$; or
(d) when both $R^1$ and $R^2$ do not equal $OR^7$, then $R^5$ is $CO_2R^7$ where $R^7$ is $$-(CH_2)_p-N\begin{matrix}(CH_2)_2\\(CH_2)_2\end{matrix}N-Ar';$$

and
Ar' is

[Structure with NH2, N, OCH3, OCH3, OCH3, $R^6$]

2-pyridine or 2,6-pyrimidine; and
p and $R^8$ are as defined previously.

Specifically preferred compounds are:

(a) 1,4-Dihydro-2,6-dimethyl-5-nitro-4-[3-(trifluoromethyl)phenyl]-[2-[4-(2-methoxyphenyl)-1-piperazinyl]ethyl]ester-3-pyridinecarboxylic acid.
(b) 1,4-Dihydro-2,6-dimethyl-4-[3-(2(4-(2-methoxyphenyl)-1-piperazinyl)ethoxy)phenyl]-5-nitro-methylester-3-pyridinecarboxylic acid.
(c) 1,4-Dihydro-2,6-dimethyl-4[2-(2-(4-(2-methoxyphenyl)-1-piperazinyl)ethoxy)phenyl]-5-nitro-methylester-3-pyridinecarboxylic acid.
(d) 1,4-Dihydro-2,6-dimethyl-4-[2-(2-(4-(2-methoxyphenyl)-1-piperazinyl)ethoxy)-3-(trifluoromethyl)-phenyl]-5-nitro-methyl-ester-3-pyridinecarboxylic acid.
(e) 1,4-Dihydro-2,6-dimethyl-4-[2-(3-(4-(2-methoxyphenyl)-1-piperazinyl)propoxy)phenyl]-5-nitro-methylester-3-pyridinecarboxylic acid.
(f) 1,4-Dihydro-2,6-dimethyl-5-nitro-4-[2-(2-(4-(2-pyrimidinyl)-1-piperazinyl)butoxy)phenyl]-methylester-3-pyridinecarboxlic acid.
(g) 1,4-Dihydro-2,6-dimethyl-4-[2-(5-(4-(2-methoxyphenyl)-1-piperazinyl)pentoxyl)phenyl]-5-nitromethylester-3-pyridinecarboxylic acid.
(h) 1,4-Dihydro-4-[2-(10-(4-(2-methoxyphenyl)1-piperazinyl)decyloxy)phenyl]-5-nitromethylester-3-pyridinecarboxylic acid.

DETAILED DESCRIPTION OF THE INVENTION

Synthesis

The dihydropyridines of the general Formula (I), according to the present invention, can be prepared by the processes illustrated below. It is understood in all of these processes that $R^1$, $R^2$, $R^3$, $R^4$, $R^5$, $R^6$, $R^6$, $R^7$, $R^8$, $R^9$, Ar, Ar', X, n, p and r have the above mentioned meanings. Methods A-E are substantially the same as the methods described in U.S. Pat. No. 4,448,964 which issued May 15, 1984.

Method A

[Scheme showing ArCHO + II + III + IV reacting to form I (dihydropyridine), and alternative route with II, IV', III']

This method is carried using the process described in H. Herbert Fox, et al., *J. Org. Chem.* 16, 1259 (1951).

The reaction is carried out in a mixture of an equal molar ratio of the starting compounds II, III, and Iv or II, III', IV' in the presence of an alcoholic solvent such as methanol, ethanol, i-propanol, n-butanol, etc., an aromatic hydrocarbon such as benzene, toluene, etc, an ether such as tetrahydrofuran (THF), dioxane, etc., a halogenated hydrocarbon such as chloroform, carbon tetrachloride, etc., an aprotic polar solvent such as acetonitrile, dimethylformamide (DMF), dimethylsulfoxide (DMSO), etc. or the like at a temperature in the range of room temperature to 200° C., preferably at 60°–110° C. Separation of the desired product from the reaction mixture is effected by conventional techniques such as filtration, concentration, extraction, column chromatography, recrystallization, etc.

Method B

[Scheme: ArCHO + II + IV' + IV + NH3 → I]

B Loev, et al., *J. Med. Chem.*, 17, 956 (1974).

The reaction is carried, out in an equal molar mixture of compounds II, IV' and IV with an equal or excess molar amount of ammonia gas or a salt thereof in the presence of a solvent using the reaction conditions described in Method A.

Method C

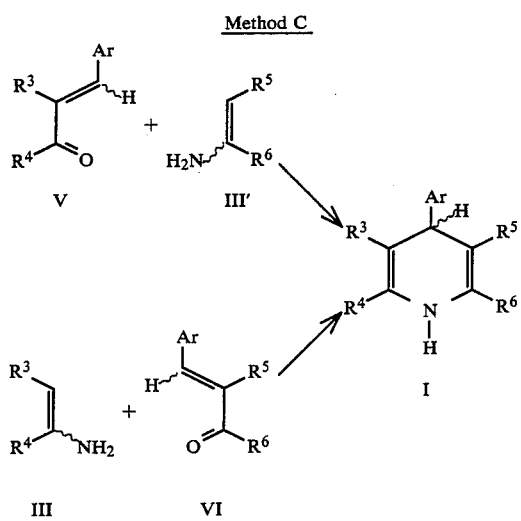

The method is carried out according to the procedure described by M. Iwanami, et. al., *Chem. Pharm. Bull.*, 27, 1426 (1979) using either compounds of Formula V and III, or III and VI as starting materials.

Method D

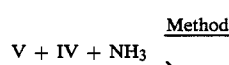

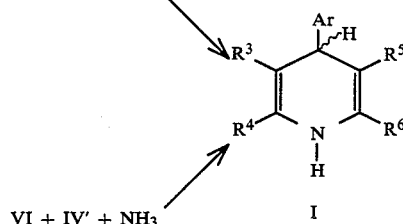

The reaction of Method D is carried out using V and IV or VI and IV, as starting materials with an equal or excess molar amount of gaseous ammonia or a salt thereof.

Method E

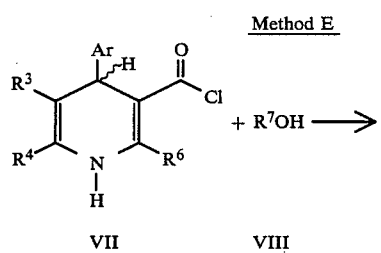

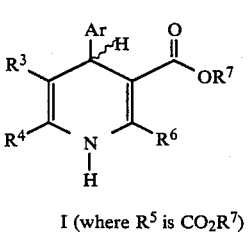

T. Shibanuma, et. al., *Chem. Pharm. Bull.* 28, 2809 (1980).

The reaction of Method E is carried out with a mixture of compounds VII and VIII in a molar ratio between 1.0:0.9 and 1.0:3.0 in a suitable solvent at a temperature in the range of −78° to 100° C., preferably at −20° to 10° C. Separation of the desired product from the reaction mixture is effected by conventional operations such as filtration, concentration, extraction, column chromatography, recrystallization, etc.

Method F

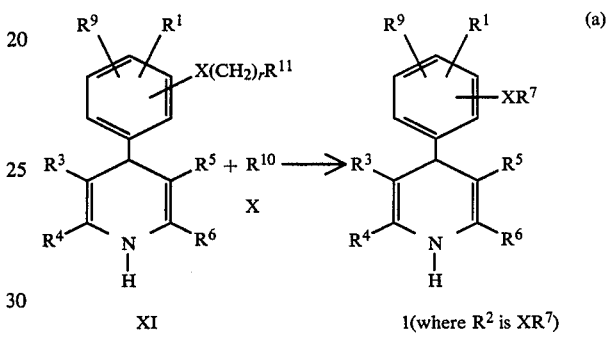

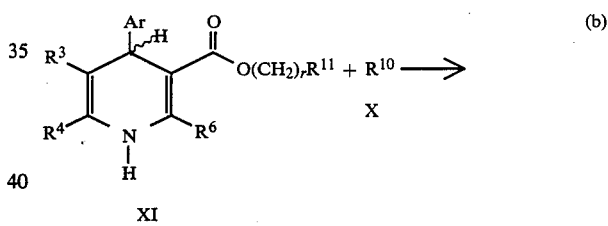

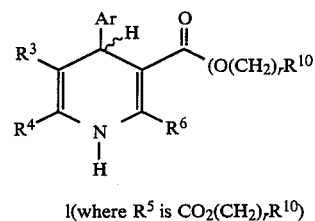

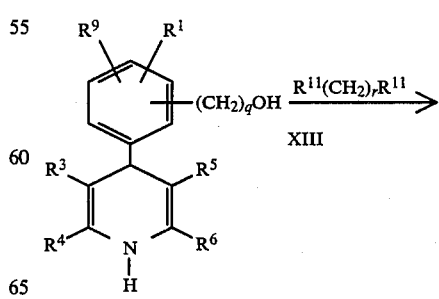

-continued
Method F

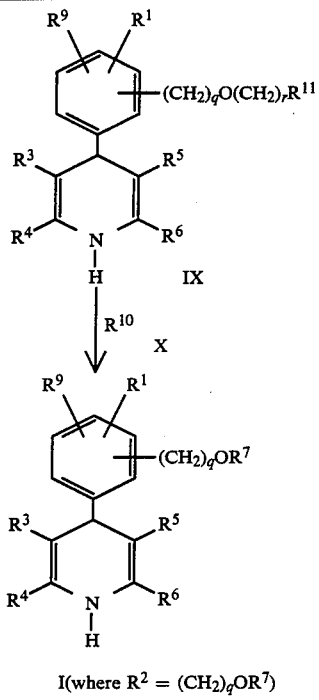

I(where $R^2 = (CH_2)_qOR^7$)

In this method $R^{10}$ is defined as $H_2N-(CH_2)_r-Y-Ar$ or

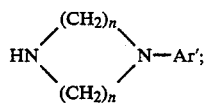

and $R^{11}$ is Br, Cl, I, tosylate (OTs), mesylate (OMs), or triflate (OTf). The reaction is carried out by reacting compounds IX and X or XI and X in a molar ratio of 1.0:1.0 to 1.0:3.0 in the presence of an alcohol such as methanol, ethanol, isopropanol, n-butanol, etc., an aromatic hydrocarbon such as benzene, toluene, etc., a halogenated hydrocarbon such as chloroform, carbon tetrachloride etc., an ether such as THF, dioxane, etc. or an aprotic solvent such as acetonitrile, DMF, DMSO, etc., at a temperature in the range of room temperature to 200° C., preferably at 100° to 150° C. Separation of the desired product from the reaction mixture is effected by conventional operations such as filtration, concentration, extraction, column chromatography, recrystallization, etc.

As shown in path (c), the anion of compound XII is generated by reacting compound XII with a base such as sodium hydride or potassium hydride in a molar ratio of 1.0:1.0 to 1.0:2.0 in the presence of an aromatic hydrocarbon such as benzene, toluene, etc., a halogenated hydrocarbon such as dichloromethane, carbon tetrachloride, etc., an ether such as THF, DME, etc., or an aprotic solvent such as acetonitrile, DMF, etc., at a temperature in the range of −20° C. to 200° C., preferably of 0° C. to 25° C. To this anion is then added XIII in a molar equivalent of 1 to 20, preferably of 2 to 4. This reaction mixture is stirred at a temperature in the range of room temperature to 200° C., preferably of 50° C. to 150° C. Separation of the desired product from the reaction mixture is effected by conventional operations such as filtration, concentration, extraction, column chromatography, recrystallization, etc. The conversion of compound IX to Compound I is described in path (a) of this method.

A resulting basic compound can be converted into a corresponding acid addition salt by reacting it with an inorganic or organic acid as is well known to one skilled in the art. Therapeutically useful acids include, for example, inorganic acids, e.g., hydrochloric, hydrobromic, sulfuric, phosphoric, nitric, etc., or organic acids, e.g., formic, acetic, propionic, succinic, maleic, tartaric, ascorbic acid, etc.

Method G

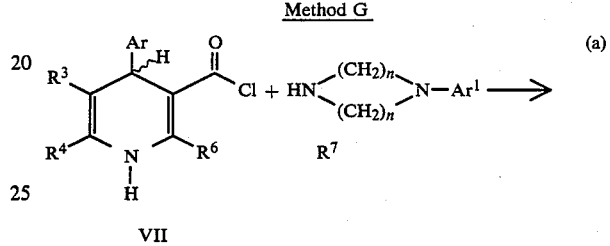 (a)

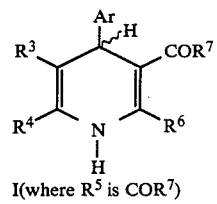

I(where $R^5$ is $COR^7$)

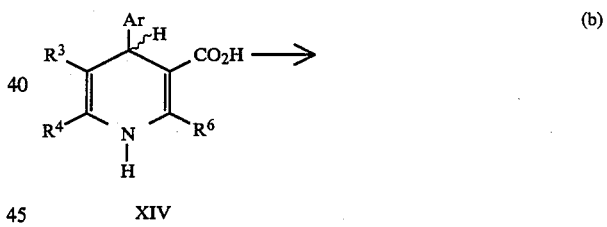 (b)

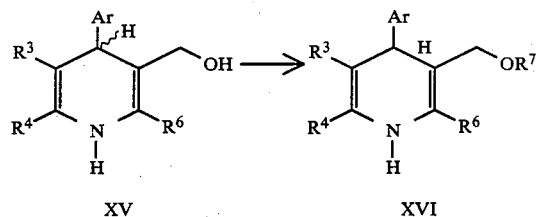

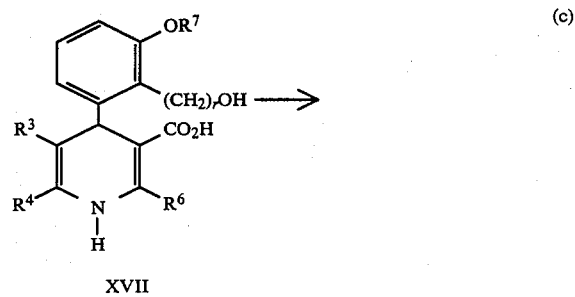 (c)

11
-continued
Method G

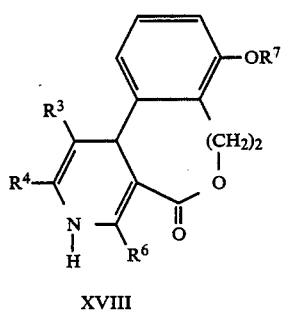

XVIII

As shown in Scheme G, path (a), to prepare compounds wherein $R^5$ is $COR^7$, a compound of formula VII can be treated with a suitable amine of formula

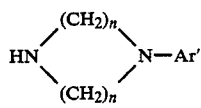

in a manner similar to that described in Method E.

As shown in path (b), the reduction of carboxylic acid XIV to allylic alcohol XV is carried out in a suitable solvent at a temperature in the range of $-78°$ C. to $100°$ C., preferably $-20°$ C. to $15°$ C., using a reducing agent such as a borane·THF complex, etc. in a molar ratio between 1.0:1.0 to 1.0:4.0. Separation of the desired product from the reaction mixture is effected by conventional operations such as filtration, concentration, extraction, column chromatography, recrystallization, etc.

Conversion of alcohol XV to compound XVI is achieved using procedures described in Method F, path (c).

As shown by path (c), the preparation of compounds where Z and $R^5$ are taken together to form a ring linked as

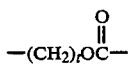

is carried out by esterification or Lactonization procedures well known to one skilled in the art such as that described in DE3235-221. The reaction is run in an ethereal solvent such as THF, dioxane, an aromatic hydrocarbon such as benzene or toluene, a halogenated hydrocarbon such as carbon tetrachloride or chloroform, or an aprotic solvent such as acetonitrile, dimethylformamide or the like at a temperature in the range of $-10°$ C. to $200°$ C., preferably at $50°-120°$ C.

The compounds of this invention and their preparation can be understood further by the following examples, but should not constitute a limitation thereof. In these examples, unless otherwise indicated, all temperatures are in degrees centigrade and parts and percentages are by weight.

12

EXAMPLE 1

Part A: Preparation of 1,4-Dihydro—2,6-dimethyl-5-nitro-4-[3-trifluoromethyl)phenyl]-(2-chloroethyl)ester-3-pyridinecarboxylic acid A mixture of 11.2 g (62.4 mmol) of 3-trifluoromethylbenzaldehyde, 6.5 g (62.4 mmol) of nitroacetone and 10 g (62.4 mmol) of 3-amino-β-chloroethyl-acetoacetate in 200 mL of absolute ethanol was stirred at room temperature under nitrogen for 36 hours. The reaction mixture was then concentrated to dryness under reduced pressure. The crude solid residue was purified by column chromatography (230–440 mesh silica gel, eluent: 70% ether in petroleum ether to 100% ether) to afford 11.1 g (43% yield) pure product as a yellow crystalline compound. $^1$H NMR (CDCl$_3$)δ: 2.32 (s, 3H); 2.51 (s, 3H); 3.62 (t, 2H); 4.30 (m, 2H); 5.45 (s, 1H); 7.01 (brs, 1H); 7.36 (t, 1H); 7.45 (d, 1H); 7.56 (d, 1H); 7.59 (s, 1H). Mass spectrum m/e 404.0737 (M+, calcd. for $C_{16}H_{16}N_2O_4F_3Cl$ 404.0750).

Part B: Preparation of 1,4-Dihydro-2,6-dimethyl-5-nitro-4-[3-(trifluoromethyl)phenyl]-[2-[4-(2-methoxyphenyl)-1-piperazinyl]ethyl]ester-3-pyridinecarboxylic acid To the mixture of 3.38 g (8.3 mmol) of the above chloride, 700 mg (8.3 mmol) of sodium bicarbonate and 30 mg of potassium iodide in 75 mL of n-butanol at room temperature under nitrogen was added 1.93 g (10.0 mmol) of 1-(o-methoxyphenyl)piperazine. The reaction mixture was refluxed for 5 hours. After cooling to room temperature, 50 mL of saturated aqueous NaCl was added to the mixture and the reaction mixture was extracted with ethyl acetate (EtOAc; 4×50 mL). The combined organic solvents were dried over magnesium sulfate (MgSO$_4$), and concentrated to give 7.2 g of a pale yellow solid which was purified by flash column chromatography (eluent: 70% ether in petroleum ether to ether) to afford 3.42 g (74% yield) of yellow crystalline product; mp $180°-183°$ C.

$^1$H NMR (CDCl$_3$)δ: 2.36 (s, 3H); 2.51 (s, 3H); 2.64 (m, 6H); 3.05 (m, 4H); 3.86 (s, 3H); 4.21 (t, 2H); 5.47 (s, 1H); 6.78–6.99 (m, 5H); 7.26–7.55 (m, 4H). Mass spectrum m/e 560.2217 (M+, calcd. for $C_{28}H_{31}H_4O_5F_3$ 560.2246).

EXAMPLE 2

Preparation of 1,4-Dihydro-2,6-Dimethyl-5-nitro-4-[2-(trifluoromethyl)phenyl]-[2-[4-(2-methoxyphenyl)-1-piperazinyl]ethyl]ester-3-pyridinecarboxylic acid.

To a stirred suspension of 1.5 g (4.3 mmol) of acid in 19 mL of dry methylene chloride at $4°$ under nitrogen was added 1.01 g (4.4 mmol) of PCl$_5$ in small portions. The reaction mixture was stirred for 1 hr. After cooling to $-15°$, a solution of 1.37 g (5.8 mmol) Of 4-(o-methoxyphenyl)-1-piperazineethanol in 5.4 mL of dry methylene chloride was added dropwise. The reaction mixture was stirred at $-15°$ to $0°$ for 3 hrs. The mixture was then washed with cold saturated aqueous sodium carbonate followed by water. The organic phase was dried (MgSO$_4$), and concentrated. The solid residue was purified by column chromatography (eluent: 20% hexane in EtOAc) to give 1.0 g of yellow solid, which was recrystallized with butyl chloride/methanol to afford 790 mg (33% yield) of product as a yellow crystalline compound; mp 125°–126°.

$^1$H NMR (CDCl$_3$)δ: 2.33 (s, 3H); 2.50 (s, 3H); 2.50–2.70 (m, 6H); 2.83–3.10 (m, 4H); 3.86 (s, 3H); 4.00–4.33 (m, 2H), 5.97 (s, $^1$H); 6.20 (s, 1H), 6.77–7.00 (m, 4H); 7.33–7.77 (m, 4H).

The compounds of Examples 1 and 2 are listed in Table 1 along with other compounds which were or can be prepared by the methods described in Examples 1 and/or 2.

TABLE 1

[Structure: dihydropyridine core with substituents R$^1$, R$^2$, R$^9$ on phenyl ring, R$^3$, R$^4$, R$^5$, R$^6$ on pyridine ring, and H on nitrogen]

| Ex. No. | R$^1$ | R$^2$ | R$^3$ | R$^4$ | R$^5$ | R$^6$ | R$^9$ | mp °C. |
|---|---|---|---|---|---|---|---|---|
| 1 | H | 3-CF$_3$ | NO$_2$ | CH$_3$ | CO$_2$CH$_2$CH$_2$N(piperazinyl)-(2-CH$_3$O-phenyl) | CH$_3$ | H | 180–183 |
| 2 | H | 2-CF$_3$ | NO$_2$ | CH$_3$ | CO$_2$CH$_2$CH$_2$N(piperazinyl)-(2-CH$_3$O-phenyl) | CH$_3$ | H | 125–126 |
| 3 | H | 2-NO$_2$ | NO$_2$ | CH$_3$ | CO$_2$CH$_2$CH$_2$N(piperazinyl)-(2-CH$_3$O-phenyl) | CH$_3$ | H | |
| 4 | H | 3-NO$_2$ | NO$_2$ | CH$_3$ | CO$_2$CH$_2$CH$_2$N(piperazinyl)-(2-CH$_3$O-phenyl) | CH$_3$ | H | |
| 5 | H | 2-Cl | NO$_2$ | CH$_3$ | CO$_2$CH$_2$CH$_2$N(piperazinyl)-(2-CH$_3$O-phenyl) | CH$_3$ | H | (glassy$^a$ solid) |
| 6 | H | 3-Cl | NO$_2$ | CH$_3$ | CO$_2$CH$_2$CH$_2$N(piperazinyl)-(2-CH$_3$O-phenyl) | CH$_3$ | H | |
| 7 | H | 2-OCH$_3$ | NO$_2$ | CH$_3$ | CO$_2$CH$_2$CH$_2$N(piperazinyl)-(2-CH$_3$O-phenyl) | CH$_3$ | H | |
| 8 | H | 3-OCH$_3$ | NO$_2$ | CH$_3$ | CO$_2$CH$_2$CH$_2$N(piperazinyl)-(2-CH$_3$O-phenyl) | CH$_3$ | 5-OCH$_3$ | |

TABLE 1-continued
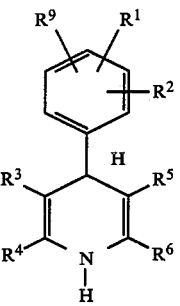
| Ex. No. | R¹ | R² | R³ | R⁴ | R⁵ | R⁶ | R⁹ | mp °C. |
|---|---|---|---|---|---|---|---|---|
| 9 | 3-CH$_3$ | 2-CF$_3$ | NO$_2$ | CH$_2$OCH$_2$CH$_2$NH$_2$ | 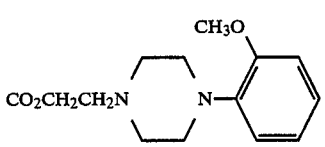 | CH$_3$ | H | |
| 10 | 3-OCH$_3$ | 2-CH$_2$F | NO$_2$ | CH$_2$OCH$_2$CH$_2$NH$_2$ | 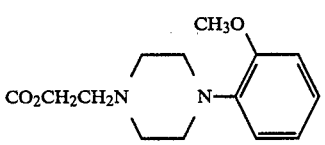 | CH$_3$ | H | |
| 11 | H | 2-CF$_3$ | NO$_2$ | CH$_2$CH(CH$_3$)$_2$ | 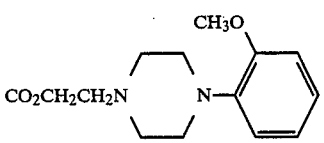 | CH$_3$ | 5-Cl | |
| 12 | H | 2-Cl | NO$_2$ | CN | 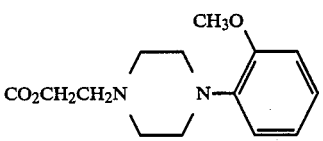 | CH$_3$ | H | |
| 13 | H | 2-CF$_3$ | NO$_2$ | CH$_3$ | 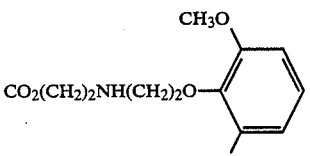 | CH$_3$ | H | 185–188 |
| 14 | H | 3-CF$_3$ | NO$_2$ | CH$_3$ | 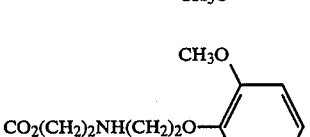 | CH$_3$ | H | |
| 15 | H | 2-NO$_2$ | NO$_2$ | CH$_3$ | 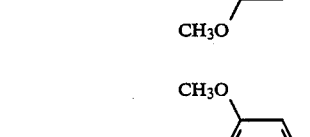 | CN | H | |

TABLE 1-continued

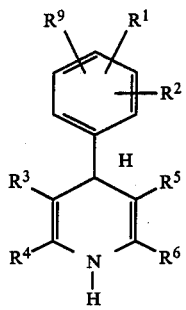

| Ex. No. | $R^1$ | $R^2$ | $R^3$ | $R^4$ | $R^5$ | $R^6$ | $R^9$ | mp °C. |
|---|---|---|---|---|---|---|---|---|
| 16 | H | 3-$NO_2$ | $NO_2$ | $CH_3$ | $CO_2(CH_2)_2NH(CH_2)_2O$-(2,6-di-$CH_3O$-phenyl) | CN | H | |
| 17 | H | 2-Cl | $NO_2$ | $CH_3$ | $CO_2(CH_2)_2NH(CH_2)_2O$-(2,6-di-$CH_3O$-phenyl) | CN | H | |
| 18 | H | 3-Cl | $NO_2$ | $CH_3$ | $CO_2(CH_2)_2NH(CH_2)_2O$-(2,6-di-$CH_3O$-phenyl) | CN | H | |
| 19 | H | 2-$OCH_3$ | $NO_2$ | $CH_3$ | $CO_2(CH_2)_2NH(CH_2)_2O$-(2,6-di-$CH_3O$-phenyl) | $CH_2OH$ | H | |
| 20 | H | 3-$OCH_3$ | $NO_2$ | $CH_3$ | $CO_2(CH_2)_2NH(CH_2)_2O$-(2,6-di-$CH_3O$-phenyl) | $CH_2OH$ | H | |
| 21 | H | 3-$CF_3$ | $NO_2$ | $CH_3$ | $CO_2(CH_2)_2NH(CH_2)_2O$-(2,6-di-$CH_3O$-phenyl) | $CH_2OH$ | H | |

TABLE 1-continued
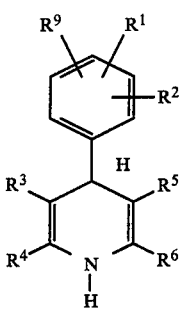
| Ex. No. | $R^1$ | $R^2$ | $R^3$ | $R^4$ | $R^5$ | $R^6$ | $R^9$ | mp °C. |
|---|---|---|---|---|---|---|---|---|
| 22 | H | 2-CF$_3$ | NO$_2$ | CH$_3$ | 4,5-dimethoxy-2-[4-(morpholinocarbonyl)piperazin-1-yl]-benzamidine-like group (OCH$_3$, OCH$_3$, NH$_2$, piperazine-CON-morpholine) | CH$_3$ | H | |
| 23 | H | 3-CF$_3$ | NO$_2$ | CH$_3$ | (same as above) | CH$_3$ | H | |
| 24 | H | 2-NO$_2$ | NO$_2$ | C$_2$H$_5$ | (same as above) | C$_2$H$_5$ | H | |
| 25 | H | 3-NO$_2$ | NO$_2$ | CH$_3$ | (same as above) | CH$_3$ | H | |
| 26 | H | 2-Cl | NO$_2$ | CH$_3$ | with CO$_2$CH$_2$N-piperazine linker | CH$_3$ | H | |

TABLE 1-continued
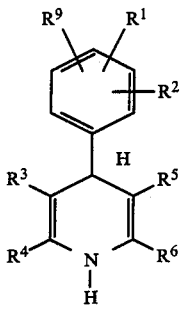
| Ex. No. | R¹ | R² | R³ | R⁴ | R⁵ | R⁶ | R⁹ | mp °C. |
|---|---|---|---|---|---|---|---|---|
| 27 | H | 3-Cl | NO₂ | CH₃ |  | CH₃ | H | |
| 28 | H | 2-OCH₃ | NO₃ | CH₃ | 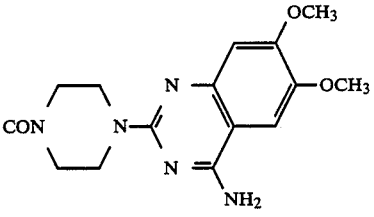 | CH₃ | H | |
| 29 | H | 3-OCH₃ | NO₂ | CH₃ | 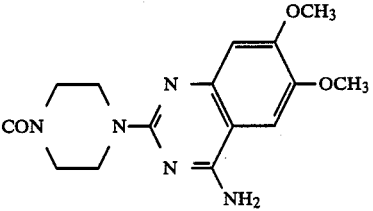 | CH₃ | H | |
| 30 | 3-CH₃ | 2-CF₃ | | 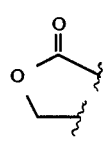 | 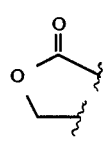 | CH₃ | H | |
| 31 | H | 2-CF₃ | | 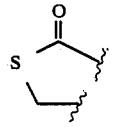 | 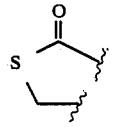 | CH₃ | H | |
| 32 | H | 2-CF₃ | | 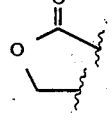 | 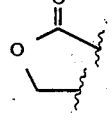 | CH₃ | H | |
| 33 | H | 3-CF₃ | | 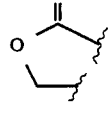 | 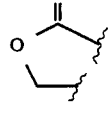 | CH₃ | H | |

TABLE 1-continued

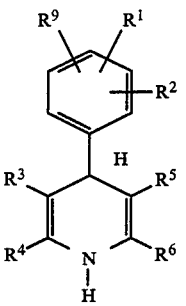

| Ex. No. | R¹ | R² | R³ | R⁴ | R⁵ | R⁶ | R⁹ | mp °C. |
|---|---|---|---|---|---|---|---|---|
| 34 | H | 2-NO$_2$ | | 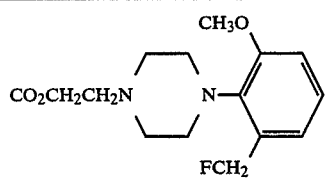 | CO$_2$CH$_2$CH$_2$N(piperazinyl)-2-OCH$_3$-6-FCH$_2$-phenyl | CH$_3$ | H | |
| 35 | H | 3-NO$_2$ | | 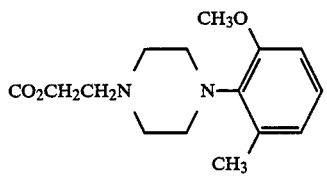 | CO$_2$CH$_2$CH$_2$N(piperazinyl)-2-OCH$_3$-6-CH$_3$-phenyl | CH$_3$ | H | |
| 36 | H | 2-Cl | | 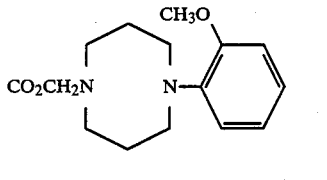 | CO$_2$CH$_2$N(homopiperazinyl)-2-OCH$_3$-phenyl | CH$_3$ | H | |
| 37 | H | 3-Cl | | 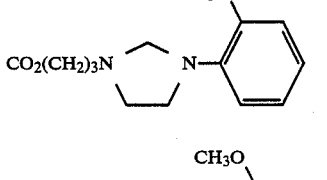 | CO$_2$(CH$_2$)$_3$N(piperazinyl)-2-OCH$_3$-phenyl | CH$_3$ | H | |
| 38 | H | 2-OCH$_3$ | | 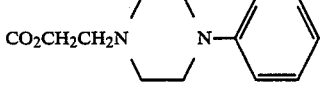 | CO$_2$CH$_2$CH$_2$N(piperazinyl)-2-OCH$_3$-phenyl | CH$_3$ | H | |
| 39 | H | 3-OCH$_3$ | | 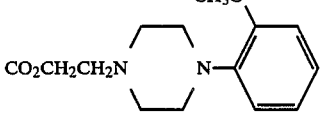 | CO$_2$CH$_2$CH$_2$N(piperazinyl)-2-OCH$_3$-phenyl | CH$_3$ | H | |
| 40 | H | 2-CF$_3$ | | 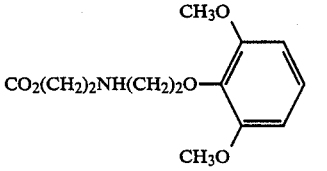 | CO$_2$(CH$_2$)$_2$NH(CH$_2$)$_2$O-2,6-(OCH$_3$)$_2$-phenyl | CH$_3$ | H | |

TABLE 1-continued

[Structure: 1,4-dihydropyridine with aryl group bearing R$^1$, R$^2$, R$^9$ substituents at the 4-position; R$^3$, R$^5$ at the 3,5-positions; R$^4$, R$^6$ at the 2,6-positions; NH in ring]

| Ex. No. | R$^1$ | R$^2$ | R$^3$ | R$^4$ | R$^5$ | R$^6$ | R$^9$ | mp °C. |
|---|---|---|---|---|---|---|---|---|
| 41 | H | 3-CF$_3$ | | (cyclic ester -O-C(=O)-CH-CH$_2$-) | CO$_2$(CH$_2$)$_2$NH(CH$_2$)$_2$S-(2,6-dimethoxyphenyl); CH$_3$O (ortho) | CH$_3$ | H | |
| 42 | H | 2-NO$_2$ | | (cyclic ester) | CO$_2$(CH$_2$)$_2$NH(CH$_2$)$_2$NH-(2,6-dimethoxyphenyl) | CH$_3$ | H | |
| 43 | H | 3-NO$_2$ | | (cyclic ester) | CO$_2$(CH$_2$)$_2$NH(CH$_2$)$_2$O-(2,6-dimethoxyphenyl) | CH$_3$ | H | |
| 44 | H | 2-Cl | | (cyclic ester) | CO$_2$CH$_2$NH(CH$_2$)$_2$O-(2,6-dimethoxyphenyl) | CH$_3$ | H | |
| 45 | H | 3-Cl | | (cyclic ester) | CO$_2$(CH$_2$)$_3$NH(CH$_2$)$_2$O-(2,6-dimethoxyphenyl) | CH$_3$ | H | |
| 46 | H | 2-OCH$_3$ | | (cyclic ester) | CO$_2$(CH$_2$)$_2$NH(CH$_2$)$_2$O-(2,6-dimethoxyphenyl) | CH$_3$ | H | |
| 47 | H | 3-OCH$_3$ | | (cyclic ester) | CO$_2$(CH$_2$)$_2$NH(CH$_2$)$_2$O-(2,6-dimethoxyphenyl) | CH$_3$ | H | |

TABLE 1-continued

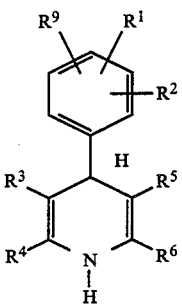

| Ex. No. | R¹ | R² | R³ | R⁴ | R⁵ | R⁶ | R⁹ | mp °C. |
|---|---|---|---|---|---|---|---|---|
| 48 | H | 2-CF₃ | | (lactone-CH) | (piperazinyl-CON, quinazoline with 2×OCH₃, NH₂) | CH₃ | H | |
| 49 | H | 3-CF₃ | | (lactone-CH) | (piperazinyl-CON, quinazoline with 2×OCH₃, NH₂) | CH₃ | H | |
| 50 | H | 2-NO₂ | | (lactone-CH) | (piperazinyl-CON, quinazoline with 2×OCH₃, NH₂) | CH₃ | H | |
| 51 | H | 3-NO₂ | | (lactone-CH) | (piperazinyl-CON, quinazoline with 2×OCH₃, NH₂) | CH₃ | H | |
| 52 | H | 2-Cl | | (lactone-CH) | (piperazinyl-CON, quinazoline with 2×OCH₃, NH₂) | CH₃ | H | |

TABLE 1-continued

[Structure: 1,4-dihydropyridine core with 4-phenyl bearing R1, R2, R9; ring positions R3, R4, R5, R6; NH]

| Ex. No. | R¹ | R² | R³ | R⁴ | R⁵ | R⁶ | R⁹ | mp °C. |
|---|---|---|---|---|---|---|---|---|
| 53 | H | 3-Cl | | | [lactone O-C(=O)-]; piperazine with CO₂CH₂N substituent, linked to triazine bearing 4,5-diOCH₃-phenyl with NH₂ | CH₃ | H | |
| 54 | H | 2-OCH₃ | | | [lactone]; piperazine (CON-) linked to triazine bearing 4,5-diOCH₃-phenyl with NH₂ | CH₃ | 6-OCH₃ | |
| 55 | H | 3-OCH₃ | | | [lactone]; piperazine (CON-) linked to triazine bearing 4,5-diOCH₃-phenyl with NH₂ | CH₃ | H | |
| 56 | H | 2-CF₃ | NO₂ | CH₃ | CO₂(CH₂)₄N-piperazinyl-N-(2-methoxyphenyl) | CH₃ | H | (glassy[b] solid) |
| 57 | H | 3-CF₃ | NO₂ | CH₃ | CO₂(CH₂)₄N-piperazinyl-N-(2-methoxyphenyl) | CH₃ | H | (glassy[c] solid) |

[a]NMR: (CDCl₃)δ 2.29 (s, 3H); 2.45 (s, 3H); 2.63 (m, 6H); 3.03 (m, 4H); 3.85 (s, 3H); 4.20 (t, 2H); 5.76 (s, 1H); 6.83–7.41 (m, 9H).
[b]Mass Spec. 589.27 (Calcd. 589.26 M + H).
[c]Mass Spec. 589.28 (Calcd. 589.26 M + H).

EXAMPLE 58

Part A: Preparation of 1,4-Dihydro-2,6-dimethyl[4-[2-(2-Chloroethoxy)]-phenyl]-5-nitro-methylester-3-pyridinecarboxylic acid The dihydropyridine can be prepared by the procedure described in Part A of Example 1 in 40% yield; mp 212°–214° C.

¹H NMR(DMSO-d₆)δ: 2.24 (s, 3H); 2.47 (s, 3H); 3.51 (s, 3H); 3.90 (t, J=5.73 Hz, 2H); 4.21 (m, 2H); 5.41 (s, 1H); 6.87 (t, J=7.31 Hz, 1H); 6.93 (d, J=8.28 Hz, 1H); 7.10 (d, J=8.74 Hz, 1H); 7.17 (t, J=7.45 Hz, 1H); 9.50 (br s, 1H).

Preparation of 1,4-Dihydro-2,6-dimethyl-[4-[2-(2-(4-(2-Methoxyphenyl)-1-piperazinyl))-ethoxy]phenyl]-5-nitro-methylester-3-pyridinecarboxylic acid To a mixture of 2.0 g (5.46 mmol) of the above dihydropyridine, 458 mg (5.46 mmol) of sodium bicarbonate and 50 mg of potassium iodide in 150 ml of n-butanol was added 1.36 g (7.09 mmol) of 1-(o-methoxyphenyl)-piperazine. The mixture was refluxed under nitrogen overnight. After cooling to room temperature, 100 ml of saturated aqueous NaCl was added. The mixture was extracted with ether (4×100ml). The combined organic solvents were dried (MgSO$_4$) and concentrated. The crude material was purified by column chromatography (eluent: 50% ether in EtOAc) to afford 1.75 g (62% yield) product as a yellow crystalline compound; mp 185°–186° C.

$^1$H NMR (DMSO-d$_6$)δ: 2.28 (s, 3H); 2.51 (s, 3H); 2.71 (m, 6H); 3.02 (m, 4H); 3.56 (s, 3H); 3.81 (s, 3H); 4.10 (m, 2H); 5.49 (s, 1H); 6.90–7.21 (m, 8H); 9.52 (br s, 1H).

EXAMPLE 59

Part A: Preparation of
1,4-dihydro-2,6-dimethyl-4-[2-(5-chloropentoxy)-phenyl]-5-nitro-methyl ester-3-pyridinecarboxylic acid The dihydropyridine was prepared by the method described in Part A of Example 1 in 32% yield (23.7 g); mp 153°–155°. $^1$H NMR (acetone d$_6$)δ: 1.58 (m, 2H); 1.80 (m, 4H); 2.27 (s, 3H); 2.47 (s, 3H); 3.53 (s, 3H); 3.67 (t, 2H); 3.93 (t, 2H); 5.52 (s, 1H); 6.79 (m, 2H); 7.10 (m, 2H); 9.34 (br s, 1H). Mass. spectrum m/e 565.32 (M+ calcd. for C$_{31}$H$_{40}$N$_4$O$_6$, 565.30).

Part B: Preparation of
1,4-dihydro-2,6-dimethyl-4[2-(5-(4-(2-methoxyphenyl)-1-piperazinyl)pentoxyl)-phenyl]-5-nitro-methyl ester-3-pyridinecarboxylic acid The product was obtained by the method described in Part B of Example 1 in 80% yield (8.5 g). $^1$H NMR (CDCl$_3$)δ: 1.70 (m, 6H); 2.26 (s, 3H); 2.40 (m, H); 2.45 (s, 3H); 2.71 (m, 4H); 3.12 (m, 4H); 3.59 (s, H); 3.85 (s, 3H); 3.90 (m, 2H); 5.57 (s, 1H); 6.50–7.50 (m, 9H). Mass spectrum m/e 565.32 (m+ calcd. for C$_{31}$H$_{40}$N$_4$O$_6$, 565.30).

EXAMPLE 60

Part A: Preparation of
1,4-dihydro-2,6-dimethyl-4-[2-(4-chlorobutoxy)-phenyl]-5-nitro-methylester-3-pyridinecarboxylic acid The dihydropyridine was prepared by the procedure described in Part A of Example 1 in 32% yield (2.5 g); mp 183–185°. 1H NMR (acetone d6)δ: 2.00 (m, H); 2.31 (s, 3H); 2.49 (s, 3H); 3.56 (s, 3H); 3.74 (m, H); 4.02 (m, 2H); 5.63 (s, 1H); 7.00 (m, 4H); 8.50 (br s, 1H). Mass spectrum m/e: 394.1271 (M+ calcd. for C$_{19}$H$_{23}$ClN$_2$O$_5$, 394.1290).

Part B: Preparation of
1,4-dihydro-2,6-dimethyl-'nitro-4-[2-(4-(4-(2-pyrimidinyl)-piperazinyl)butoxy)phenyl]methylester-36pyridinecarboxylic acid The product was obtained in 82% yield (1.5 g) using the procedure described in Part B of Example 58. $^1$H NMR (CDCl$_3$)δ: 1.70 (m, 4H); 2.25 (s, 3H); 2.50 (s, H); 2.57 (m, 6H) 3.54 (m, 4H); 3.59 (s, 3H); 3.93 (m, H); 5.58 (s, 1H); 6.59 (t, 2H); 6.80 (t, 2H); 7.11 (t, 1H); 7.27 (d, 1H); 7.47 (t, 1H); 7.85 (s, 1H); 8.19 (d, 2H). Mass spectrum m/e: 523.27 (m+ calcd. for C$_{27}$H$_{34}$N$_6$O$_5$4, 523.27).

EXAMPLE 61

Preparation of
1,4-dihydro-2,6-dimethyl-4-[2(10-bromodecyloxy)-phenyl]-5-nitro-methyl ester-3-pyridinecarboxylic acid The dihydropyridine was prepared by the procedure described in Part A of Example 1 in 27% yield (2.7 g); mp 122°–125°. $^1$H NMR (acetone d$^6$)δ: 1.35 (m, H); 2.05 (m, 2H); 2.29 (s, 3H); 2.48 (s, 3H); 3.56 (s, 3H); 3.57 (m, 2H); 3.95 (t, 2H); 5.59 (s, 1H); 6.73–7.30 (m, 4H); 8.46 (br s, 1H). Mass spectrum m/e: 523.18 (m+ calcd. for C$_{25}$H$_{35}$BrN$_2$O$_5$, 523.18).

Part B: Preparation of
1,4-dihydro-2,6-dimethyl-4[2(10-(4-(2-methoxyphenyl)-piperazinyl)decyloxy)phenyl]-5-nitro-methyl ester-3-pyridinecarboxylic acid The product was prepared in 81% yield (1.7 g) using the procedure described in Part B of Example 58. $^1$H NMR (CDCl$_3$)δ: 1.31 (m, 16H); 2.26 (s, 3H); 2.28 (m, 2H); 2.44 (s, 3H); 2.65 (m, 4H); 3.11 (m, 4H); 3.59 (s, 3H); 3.85 (s, 3H); 3.88 (m, 2H); 5.60 (s, 1H); 6.45 (br s, 1H); 6.70–7.30 (m, 8H). Mass spectrum m/e: 635.46 (M+ calcd. for C$_{36}$H$_{50}$N$_{4.6}$, 635.38).

EXAMPLE 62

Part A: Preparation of
[4-[3-(3-chloropropoxy)phenyl]]-2-methyl-5-oxo-1,4,5,tetrahydrofuro[3,4-b]-methylester-3-pyridinecarboxylic acid The dihydropyridine lactone was prepared by the procedure described by S. D. Young, Synthesis, 617–618, 1984 from the corresponding 4-aryl-2,6-dimethyl-1,4-dihydropyridine-3,5-dimethylcarboxylate in 42% yield (0.42 g). $^1$H NMR (CDCl$_3$)δ: 2.18 (t, 2H); 2.34 (s, 3H); 3.58 (s, 3H); 3.70 (t, 2H); 4.05 (t, 2H); 4.54 (d, 2H); 4.84 (s, 1H); 6.68 (d, 1H); 6.80 (d, 2H); 7.16 (t, 1H); 8.18 (br s, 1H).

PART B: Preparation of
[4-(3-(3-4-(2-methoxyphenyl)-1

Part B: Preparation of
[4-(3-(3-4-(2-methoxyphenyl)-1-piperazinyl)propoxy))-phenyl]-2-methyl-5-oxo-1,4,5,7-tetrahydrofuro[3,4-b]-methylester-3-pyridinecarboxylic acid This product was prepared by the same procedure described in Example 58 Part B (72% yield, g). $^1$H NMR (CDCl$_3$)δ: 2.02 (s, 3H); 2.60 (m, 6H); 3.08 (m, 4H); 3.55 (s, 3H); 3.85 (s, 3H); 4.0 (t, 2H); 4.71 (s, 2H); 4.80 (s, 1H); 6.71 (d, 1H); 6.91 (m, 6H); 7.14 (t, 1H); 9.37 (br s, 1H).

Compounds listed in Table 2 were prepared or can be prepared using the methods described in Examples 58–62 and by the methods described hereinabove.

TABLE 2

[Structure: dihydropyridine with R1-R9 substituents on phenyl and pyridine rings]

| Ex. No. | R¹ | R² | R³ | R⁴ | R⁵ | R⁶ | R⁹ | mp °C. |
|---|---|---|---|---|---|---|---|---|
| 58 | H | 2-OCH₂CH₂N(piperazine)-(2-methoxyphenyl) | NO₂ | CH₃ | CO₂CH₃ | CH₃ | H | 185–186 |
| 59 | H | 2-O(CH₂)₅N(piperazine)-(2-methoxyphenyl) | NO₂ | CH₃ | CO₂CH₃ | CH₃ | H | (glassy solid) |
| 60 | H | 2-O(CH₂)₄N(piperazine)-(2-pyrimidinyl) | NO₂ | CH₃ | CO₂CH₃ | CH₃ | H | (glassy solid) |
| 61 | H | 2-O(CH₂)₁₀N(piperazine)-(2-methoxyphenyl) | NO₂ | CH₃ | CO₂CH₃ | CH₃ | H | (glassy solid) |
| 62 | H | 3-O(CH₂)₃N(piperazine)-(2-methoxyphenyl) | [ester linkage structure] | | CO₂CH₃ | CH₃ | H | (glassy solid) |

TABLE 2-continued

| | | | | | | | |
|---|---|---|---|---|---|---|---|
| 63 | H | 3-O(CH₂)₄N-[2-CH₃O-phenyl-piperazine] | (lactone) | CO₂CH₃ | CH₃ | H | (glassy[rr] solid) |
| 64 | H | 2-OCH₂CH₂N-[2-CH₃O-phenyl-piperazine] | CH₃ / NO₂ | CO₂Et | CH₃ | H | |
| 65 | H | 2-OCH₂CH₂N-[2-CH₃O-phenyl-piperazine] | (lactone) | CO₂Et | CH₃ | H | |
| 66 | H | 2-OCH₂CH₂N-[2-CH₃O-phenyl-piperazine] | CH₃ / NO₂ | CO₂iPr | CH₃ | H | |
| 67 | H | 2-OCH₂CH₂N-[2-CH₃O-phenyl-piperazine] | (lactone) | CO₂iPr | CH₃ | H | |
| 68 | 6-NO₂ | 3-OCH₂CH₂N-[2-CH₃O-phenyl-piperazine] | CH₃ / NO₂ | CO₂CH₃ | CH₃ | H | 104–106 |
| 69 | H | 3-OCH₂CH₂N-[2-CH₃O-phenyl-piperazine] | CH₃ / NO₂ | CO₂CH₃ | CH₃ | H | (glassy[a] solid) |

TABLE 2-continued

| # | R1 | Ar | R2 | R3 | R4 | R5 |
|---|----|----|----|----|----|-----|
| 70 | H | 3-OCH₂CH₂N-piperazine-(2-OCH₃-phenyl) | -C(=O)-O-CH₂- (cyclic) | CO₂CH₃ | CH₃ | H |
| 71 | H | 3-OCH₂CH₂N-piperazine-(2-OCH₃-phenyl) | CH₃ / NO₂ | NO₂ | CH₃ | H |
| 72 | H | 3-OCH₂CH₂N-piperazine-(2-OCH₃-phenyl) | -C(=O)-O-CH₂- (cyclic) | CO₂Et | CH₃ | H |
| 73 | H | 3-OCH₂CH₂N-piperazine-(2-OCH₃-phenyl) | CH₃ / NO₂ | iPr-O-C(=O)- | CH₃ | H |
| 74 | H | 3-OCH₂CH₂N-piperazine-(2-OCH₃-phenyl) | -C(=O)-O-CH₂- (cyclic) | iPr-O-C(=O)- | CH₃ | H |
| 75 | 3-OCH₃ | 2-OCH₂CH₂N-piperazine-C(=N)(NH₂)-(4,5-di-OCH₃-phenyl) | NO₂ | CO₂CH₃ | CH₃ | H |

TABLE 2-continued

| | | | | | |
|---|---|---|---|---|---|
| 76 | 3-OCH₃ | 4,5-di-OCH₃ aryl w/ NH₂, 2-OCH₂CH₂N-piperazine | (cyclic ester/lactone) | CO₂CH₃ | CH₃ | H |
| 77 | 3-Cl | 4,5-di-OCH₃ aryl w/ NH₂, 2-OCH₂CH₂N-piperazine | NO₂ CH₃ | CO₂Et | CH₃ | 5-Cl |
| 78 | 3-Cl | 4,5-di-OCH₃ aryl w/ NH₂, 2-OCH₂CH₂N-piperazine | (cyclic ester/lactone) | CO₂Et | CH₃ | H |
| 79 | 3-CF₃ | 4,5-di-OCH₃ aryl w/ NH₂, 2-OCH₂CH₂N-piperazine | NO₂ CH₃ | CO₂iPr | CH₃ | H |

TABLE 2-continued

| # | Structure | R | R' | R'' | R''' |
|---|---|---|---|---|---|
| 80 | 4,5-di-OCH₃ phenyl amidine, piperazine with 2-OCH₂CH₂N, 3-OCH₃ | CH₃-C(=O)-O-CH₂CH₃ (ethyl acetate group) | CH(CH₃)-CO₂- (isopropyl ester) | CH₃ | H |
| 81 | 4,5-di-OCH₃ phenyl amidine, piperazine with 3-OCH₂CH₂N | NO₂ | CH₃ | CO₂CH₃ | H |
| 82 | 4,5-di-OCH₃ phenyl amidine, piperazine with 3-OCH₂CH₂N | ester linkage (O-C(=O)-CH(-)CH₂CH₃) | | CO₂CH₃ | C₃H₇ | H |
| 83 | 4,5-di-OCH₃ phenyl amidine, piperazine with 3-OCH₂CH₂N | NO₂ | CH₃ | CO₂Et | CH₂O(CH₂)₂NH₂ | H |
| 84 | 2-OCH₃ phenyl, piperazine with 2-O(CH₂)₅N | NO₂ | CH₃ | CO₂CH₃ | CH₂O(CH₂)₂NH₂ | H (glassy[pp] solid) |

TABLE 2-continued

| # | Ar1 | R | R' | R'' | R''' | mp |
|---|---|---|---|---|---|---|
| 85 | 2-CF₃ | 3,4-dimethoxyphenyl-amidine with 3-OCH₂CH₂N-piperidinyl | NO₂ | CH₃ | CO₂(iPr) | CH₂O(CH₂)₂NH₂ | H |
| 86 | 2-CF₃ | 3,4-dimethoxyphenyl-amidine with 3-OCH₂CH₂N-piperidinyl | (ethyl ester linker) | | CH₂O(CH₂)₂NH₂ | H |
| 87 | 3-OCH₃ | 2-CH₃O-phenyl-N-piperidinyl with 2-OCH₂CH₂CH₂N | NO₂ | CH₃ | CO₂CH₃ | CH₃ | H (glassy[b] solid) |
| 88 | H | 2-CH₃O-phenyl-N-piperidinyl with 2-OCH₂CH₂CH₂N | NO₂ | CH₃ | CO₂CH₃ | CH₃ | H 150–151.5 |
| 89 | H | 2-OCH₃-phenyl-N-piperidinyl with 3-OCH₂CH₂CH₂N | NO₂ | CH₃ | | CH₃ | H 149–150 |
| 90 | H | 2-Cl-phenyl-N-piperidinyl with 2-OCH₂CH₂N | NO₂ | CH₃ | CO₂CH₃ | CH₃ | H |

TABLE 2-continued
| | | | | | | | |
|---|---|---|---|---|---|---|---|
| 91 | H | 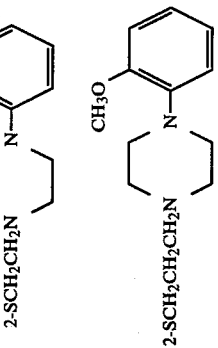 | NO₂ | CH₃ | CO₂CH₃ | CH₃ | H |
| 92 | H | 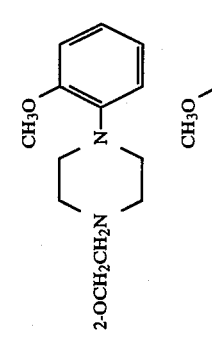 | NO₂ | CH₃ | CO₂CH₃ | CH₃ | H |
| 93 | 3-CH₃ | 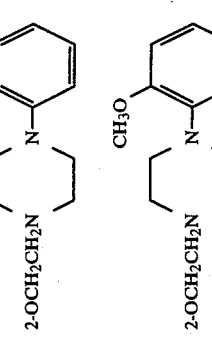 | NO₂ | CH₃ | CO₂CH₃ | CH₃ | H |
| 94 | 3-Cl | 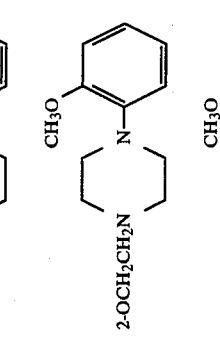 | NO₂ | CH₃ | CO₂CH₃ | CH₃ | H |
| 95 | 3-OC₂H₅ | 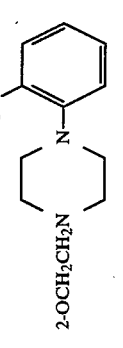 | NO₂ | CH₃ | CO₂CH₃ | CH₃ | H |
| 96 | 3-NO₂ |  | NO₂ | CH₃ | CO₂CH₃ | CH₃ | H |
| 97 | 3-CF₃ |  | NO₂ | CH₃ | CO₂CH₃ | CH₃ | H |

TABLE 2-continued

| No. | Structure | | | | | | mp |
|---|---|---|---|---|---|---|---|
| 98 | 2-NO2 | [piperazine with 2-CH3O-phenyl, 3-OCH2CH2N] | NO2 | CH3 | CO2CH3 | CH3 | H | |
| 99 | 3-OCCH3 (=O) | [piperazine with 2-CH3O-phenyl, 2-OCH2CH2N] | NO2 | CH3 | CO2CH3 | CH3 | H | |
| 100 | 3-CH3 | [piperazine with 2-CH3O-phenyl, 2-NHCH2CH2N] | NO2 | CH3 | CO2CH3 | CH3 | H | |
| 101 | 5-F | [piperazine with 2-CH3O-phenyl, 2-OCH2CH2N] | NO2 | CH3 | CO2CH3 | CH3 | H | |
| 102 | 2-OCH2F | [piperazine with 2-CH3O-phenyl, 3-OCH2CH2N] | NO2 | CH3 | CO2CH3 | CH3 | H | |
| 103 | 5-Br | [piperazine with 2-CH3O-phenyl, 3-OCH2CH2N] | NO2 | CH3 | CO2CH3 | CH3 | H | |
| 104 | H | [piperazine with 2-CF3-phenyl, 2-O(CH2)3N] | NO2 | CH3 | CO2CH3 | CH3 | H | 163–164 |

TABLE 2-continued

| # | R | Structure | | | | | Notes |
|---|---|---|---|---|---|---|---|
| 105 | H | 2-O(CH₂)₄N-piperidine-(2-OCH₃-phenyl) | NO₂ | CH₃ | CO₂CH₃ | H | (glassy solid)[c] |
| 106 | 3-OCH₃ | 2-O(CH₂)₃N-piperidine-(2-OCH₃-phenyl) | NO₂ | CH₃ | CO₂CH₃ | H | (glassy solid)[d] |
| 107 | H | 3-O(CH₂)₄N-piperidine-(2-OCH₃-phenyl) | NO₂ | CH₃ | CO₂CH₃ | H | (glassy solid)[e] |
| 108 | 3-OC₂H₅ | 2-O(CH₂)₃N-piperidine-(2-OCH₃-phenyl) | NO₂ | CH₃ | CO₂CH₃ | H | (glassy solid)[f] |
| 109 | 3-OC₂H₅ | 2-O(CH₂)₄N-piperidine-(2-OCH₃-phenyl) | NO₂ | CH₃ | CO₂CH₃ | H | (glassy solid)[g] |
| 110 | 3-OCH₃ | 2-O(CH₂)₄N-piperidine-(2-OCH₃-phenyl) | NO₂ | CH₃ | CO₂CH₃ | H | (glassy solid)[h] |
| 111 | 3-OCH₃ | 2-O(CH₂)₅N-piperidine-(2-OCH₃-phenyl) | NO₂ | CH₃ | CO₂CH₃ | H | (glassy solid)[i] |

TABLE 2-continued

| No. | | | | | | | | mp |
|---|---|---|---|---|---|---|---|---|
| 112 | 3-OC$_2$H$_5$ | [2-O(CH$_2$)$_5$N-piperidine-N-(2-CH$_3$O-phenyl)] | NO$_2$ | CH$_3$ | CO$_2$CH$_3$ | CH$_3$ | H | (glassy solid)[j] |
| 113 | H | [3-O(CH$_2$)$_5$N-piperidine-N-(2-CH$_3$O-phenyl)] | NO$_2$ | CH$_3$ | CO$_2$CH$_3$ | CH$_3$ | H | (glassy solid)[k] |
| 114 | 3-OCH$_3$ | [2-O-CH$_2$CH=CHCH$_2$-N-piperazine-N-(2-CH$_3$O-phenyl)] | NO$_2$ | CH$_3$ | CO$_2$CH$_3$ | CH$_3$ | H | (glassy solid)[l] |
| 115 | H | [2-O(CH$_2$)$_4$N-piperidine-N-(2-CH$_3$O-phenyl)] | NO$_2$ | CH$_3$ | CONHPh | CH$_3$ | H | (glassy solid)[m] |
| 116 | H | [2-O(CH$_2$)$_4$N-pyridyl] | NO$_2$ | CH$_3$ | CO$_2$CH$_3$ | CH$_3$ | H | (glassy solid)[n] |
| 117 | H | [3-O(CH$_2$)$_3$N-piperidine-N-(2-CH$_3$O-phenyl)] | NO$_2$ | CH$_3$ | CO$_2$Et | CH$_3$ | H | (glassy solid)[o] |
| 118 | H | [2-O(CH$_2$)$_4$N-piperidine-N-(2-CH$_3$-phenyl)] | NO$_2$ | | CO$_2$CH$_3$ | CH$_3$ | H | 114–117 |

TABLE 2-continued

| | | | | | | | | |
|---|---|---|---|---|---|---|---|---|
| 119 | H | [2-CH3O-phenyl-piperazine-(CH2)-CH=CH-CH2-O-, 2-O] | NO2 | CH3 | CO2CH3 | CH3 | H | (glassy[p] solid) |
| 120 | H | [2-CH3O-phenyl-piperazine-(CH2)4-O-, 2-O] | NO2 | CH3 | CO2Et | CH3 | H | 133–135 |
| 121 | 3-OCH3 | [pyrimidine-piperazine-(CH2)-CH=CH-CH2-O-, 2-O] | NO2 | CH3 | CO2CH3 | CH3 | H | glassy[q] solid |
| 122 | H | [2-CH3O-phenyl-piperazine-(CH2)3-O-, 3-O] | NO2 | CH3 | CONHPh | CH3 | H | 132–134 |
| 123 | H | [bis(4-F-phenyl)CH-piperazine-(CH2)3-O-, 3-O] | NO2 | CH3 | CO2CH3 | CH3 | H | (glassy[r] solid) |
| 124 | H | [pyrimidine-piperazine-(CH2)3-O-, 3-O] | NO2 | CH3 | CO2CH3 | CH3 | H | 193–194.5 |
| 125 | H | [2-CH3O-phenyl-piperazine-(CH2)-CH=CH-CH2-O-, 3-O] | NO2 | CH3 | CO2CH3 | CH3 | H | (glassy[s] solid) |

TABLE 2-continued

| # | | Ar-group | | | | mp (°C) |
|---|---|---|---|---|---|---|
| 126 | H | 3-O(CH₂)₃N-piperazine-(2-pyridyl) | NO₂ | CH₃ | CO₂Et | H | 131–133 |
| 127 | H | 3-O-(but-2-ynyl)-N-piperazine-(2-OCH₃-phenyl) | NO₂ | CH₃ | CO₂CH₃ | H | (glassy[t] solid) |
| 128 | H | 3-O(CH₂)₃N-piperazine-(2-pyridyl) | NO₂ | CH₃ | CO₂CH₃ | H | 146–149 |
| 129 | H | 2-O(CH₂)₆N-piperazine-(2-OCH₃-phenyl) | NO₂ | CH₃ | CO₂CH₃ | H | 138–141 |
| 130 | H | 3-O(CH₂)₃N-piperazine-(2-OCH₃-phenyl) | NO₂ | CH₃ | CO₂CH₃ | H | 137–140 |
| 131 | H | 3-O(CH₂)₃N-piperazine-(2-CH₃-phenyl) | NO₂ | CH₃ | CO₂CH₃ | H | (glassy[u] solid) |
| 132 | H | 3-O(CH₂)₃N-piperazine-(2-Cl-phenyl) | NO₂ | CH₃ | CO₂CH₃ | H | (glassy[v] solid) |

TABLE 2-continued

| | Structure | | | | | | |
|---|---|---|---|---|---|---|---|
| 133 | 2-O(CH₂)₄N-piperidine-C₆H₄-OCH₃(2) | H | NO₂ | CH₃ | CO₂iPr | CH₃ | H | 174–175.5 |
| 134 | 2-O(CH₂)₃N-piperidine-C₆H₄-OCH₃(2) | H | NO₂ | CH₃ | CO₂iPr | CH₃ | H | (glassy[w] solid) |
| 135 | 4-O(CH₂)₃N-piperidine-C₆H₄-OCH₃(2) | H | NO₂ | CH₃ | CO₂CH₃ | CH₃ | H | (glassy[x] solid) |
| 136 | 3-O-CH₂-oxirane-CH₂-N-piperazine-C₆H₄-OCH₃(2) | H | NO₂ | CH₃ | CO₂CH₃ | CH₃ | H | 164–166 |
| 137 | 4-O(CH₂)₃N-piperidine-C₆H₄-OCH₃(2) | 3-NO₂ | NO₂ | CH₃ | CO₂CH₃ | CH₃ | H | (glassy[y] solid) |
| 138 | 2-O(CH₂)₄N-piperidine-C₆H₄-OCH₃(2) | 5-NO₂ | NO₂ | CH₃ | CO₂CH₃ | CH₃ | H | glassy[z] solid) |
| 139 | 2-O(CH₂)₃N-piperidine-C₆H₄-OCH₃(2) | 3-NO₂ | NO₂ | CH₃ | CO₂CH₃ | CH₃ | H | (glassy[aa] solid) |

TABLE 2-continued

| # | Structure | | | | | mp |
|---|---|---|---|---|---|---|
| 140 | 3-NO$_2$ 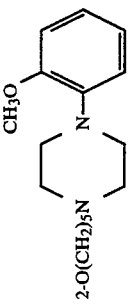 2-O(CH$_2$)$_5$N | NO$_2$ | CH$_3$ | CO$_2$CH$_3$ | CH$_3$ | H | (glassy[bb] solid) |
| 141 | 3-Cl 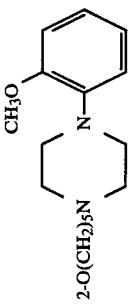 2-O(CH$_2$)$_5$N | NO$_2$ | CH$_3$ | CO$_2$CH$_3$ | CH$_3$ | 5 Cl | (glassy[cc] solid) |
| 142 | 5-Br 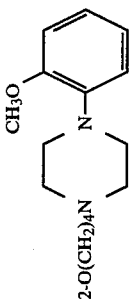 2-O(CH$_2$)$_4$N | NO$_2$ | CH$_3$ | CO$_2$CH$_3$ | CH$_3$ | H | 184–186 |
| 143 | 5-Cl 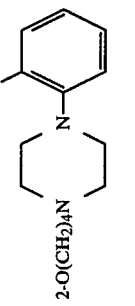 2-O(CH$_2$)$_4$N | NO$_2$ | CH$_3$ | CO$_2$CH$_3$ | CH$_3$ | H | 183–185 |
| 144 | CH$_2$=CHCH$_2$- 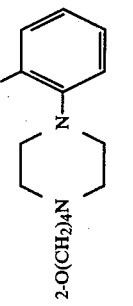 2-O(CH$_2$)$_4$N | NO$_2$ | CH$_3$ | CO$_2$CH$_3$ | CH$_3$ | H | (glassy[dd] solid) |
| 145 | 5-Cl 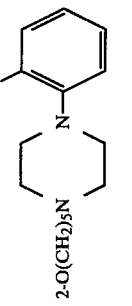 2-O(CH$_2$)$_5$N | NO$_2$ | CH$_3$ | CO$_2$CH$_3$ | CH$_3$ | H | (glassy[ee] solid) |
| 146 | H 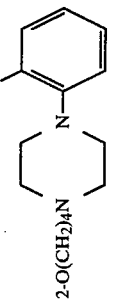 2-O(CH$_2$)$_4$N | NO$_2$ | CH$_3$ | CO$_2$tBu | CH$_3$ | H | (glassy[ff] solid) |

TABLE 2-continued

| No. | Structure | Chain | | | | | mp |
|---|---|---|---|---|---|---|---|
| 147 | 3-NO₂ | 2-O(CH₂)₄N | NO₂ | CH₃ | CO₂CH₃ | CH₃ | H | (glassy solid) |
| 148 | 3-NO₂ | 2-O(CH₂)₆N | NO₂ | CH₃ | CO₂CH₃ | CH₃ | H | (glassy solid) |
| 149 | 2-NO₂ | 3-O(CH₂)₃N | NO₂ | CH₃ | CO₂CH₃ | CH₃ | H | (glassy$^{gg}$ solid) |
| 150 | 2-NO₂ | 3-O(CH₂)₄N | NO₂ | CH₃ | CO₂CH₃ | CH₃ | H | (glassy$^{hh}$ solid) |
| 151 | 2-NO₂ | 3-O(CH₂)₅N | NO₂ | CH₃ | CO₂CH₃ | CH₃ | H | (glassy$^{ii}$ solid) |
| 152 | 5-OCH₃ | 2-O(CH₂)₄N | NO₂ | CH₃ | CO₂CH₃ | CH₃ | H | 141–145 |
| 153 | 5-OCH₃ | 2-O(CH₂)₅N | NO₂ | CH₃ | CO₂CH₃ | CH₃ | H | 138.5–141.5 |

Common structure: 2-methoxyphenyl-N-piperidine attached via O(CH₂)ₙ chain

TABLE 2-continued

| # | | | | | | | |
|---|---|---|---|---|---|---|---|
| 154 | H | 2-O(CH$_2$)$_2$N-piperazinyl-pyrimidine | NO$_2$ | CH$_3$ | CO$_2$CH$_3$ | CH$_3$ | H (glassy$^{jj}$ solid) |
| 155 | H | 2-O(CH$_2$)$_5$N-piperazinyl-pyrimidine | NO$_2$ | CH$_3$ | CO$_2$CH$_3$ | CH$_3$ | H (glassy$^{kk}$ solid) |
| 156 | H | 3-O(CH$_2$)$_3$N-piperazinyl-pyrimidine | NO$_2$ | CH$_3$ | CONHPh | CH$_3$ | H (glassy$^{ll}$ solid) |
| 157 | H | 3-O(CH$_2$)$_6$N-piperazinyl-pyrimidine | NO$_2$ | CH$_3$ | CO$_2$CH$_3$ | CH$_3$ | H (glassy$^{mm}$ solid) |
| 158 | 2-NO$_2$ | 3-O(CH$_2$)$_3$N-piperazinyl-pyrimidine | NO$_2$ | CH$_3$ | CO$_2$CH$_3$ | CH$_3$ | H |
| 159 | 2-NO$_2$ | 3-O(CH$_2$)$_4$N-piperazinyl-pyrimidine | NO$_2$ | CH$_3$ | CO$_2$CH$_3$ | CH$_3$ | H |
| 160 | 2-NO$_2$ | 3-O(CH$_2$)$_5$N-piperazinyl-pyrimidine | NO$_2$ | CH$_3$ | CO$_2$CH$_3$ | CH$_3$ | H |
| 161 | 2-NO$_2$ | 3-O(CH$_2$)$_6$N-piperazinyl-pyrimidine | NO$_2$ | CH$_3$ | CO$_2$CH$_3$ | CH$_3$ | H |

TABLE 2-continued
| | | | | | | |
|---|---|---|---|---|---|---|
| 162 | 3-OCH$_3$ | 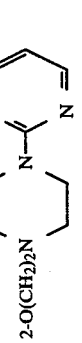 2-O(CH$_2$)$_2$N | NO$_2$ | CH$_3$ | CO$_2$CH$_3$ | CH$_3$ | H | (glassy[qq] solid) |
| 163 | 3-NO$_2$ | 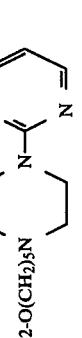 2-O(CH$_2$)$_5$N | NO$_2$ | CH$_3$ | CO$_2$CH$_3$ | CH$_3$ | H |
| 164 | 3-cf$_3$ | 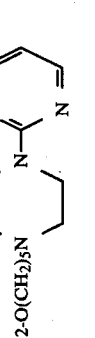 2-O(CH$_2$)$_5$N | NO$_2$ | CH$_3$ | CO$_2$Et | CH$_3$ | 5-NO$_2$ |
| 165 | 3-Cl |  2-O(CH$_2$)$_4$N | NO$_2$ | CH$_3$ | CO$_2$CH$_3$ | CH$_3$ | 6-Cl |
| 166 | H | 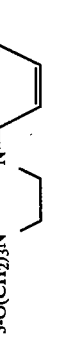 3-O(CH$_2$)$_3$N | NO$_2$ | CH$_3$ | 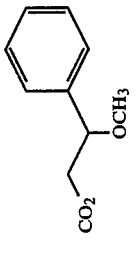 | CH$_3$ | H |
| 167 | H | 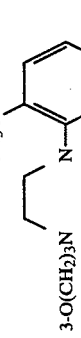 4-O(CH$_2$)$_4$N | NO$_2$ | CH$_3$ |  | CH$_3$ | H |
| 168 | H | 3-O(CH$_2$)$_3$N | CN | CH$_3$ | CO$_2$CH$_3$ | CH$_3$ | H | (glassy[nn] solid) |

TABLE 2-continued

| # | | Structure | | | | | | Notes |
|---|---|---|---|---|---|---|---|---|
| 169 | H | 3-O(CH$_2$)$_4$N–[piperazine]–[phenyl-2-OCH$_3$] | CN | CH$_3$ | CO$_2$CH$_3$ | CH$_3$ | H | (glassy solid)$^{ss}$ |
| 170 | H | 2-O(CH$_2$)$_4$N–[piperazine]–[phenyl-2-OCH$_3$] | CN | CH$_3$ | CO$_2$CH$_3$ | CH$_3$ | H | (glassy solid)$^{tt}$ |
| 171 | H | 3-O(CH$_2$)$_4$N–[piperazine]–[pyrimidinyl] | CN | CH$_3$ | CO$_2$CH$_3$ | CH$_3$ | H | (glassy solid)$^{uu}$ |
| 172 | 3-CF$_3$ | 2-O(CH$_2$)$_4$N–[piperazine]–[phenyl-2-OCH$_3$] | CN | CH$_3$ | CO$_2$CH$_3$ | CH$_3$ | H | |
| 173 | H | 3-O(CH$_2$)$_3$N–[piperazine]–[pyrimidinyl] | CN | CH$_3$ | CO$_2$CH$_3$ | CH$_3$ | H | (glassy solid)$^{vv}$ |
| 174 | H | 3-O(CH$_2$)$_3$N–[piperazine]–[phenyl-2-OCH$_3$] | CONH$_2$ | CH$_3$ | CO$_2$CH$_3$ | CH$_3$ | H | |
| 175 | H | 2-O(CH$_2$)$_5$N–[piperazine]–[phenyl-2-OCH$_3$] | CONH$_2$ | CH$_3$ | CO$_2$CH$_3$ | CH$_3$ | H | |

TABLE 2-continued

| # | Structure | | | | | | |
|---|---|---|---|---|---|---|---|
| 176 | 3-NO2 | 2-OCH3-C6H4-N(piperazine)-2-O(CH2)4N | CONH2 | CH3 | CO2CH3 | CH3 | H |
| 177 | H | 2-OCH3,6-OCH3-C6H3-N(piperazine)-2-CH2O(CH2)3N | NO2 | CH3 | CO2CH3 | CO2CH3 | H |
| 178 | H | 2-OCH3-C6H4-N(piperazine)-2-(CH2)2O(CH2)2N | NO2 | CH3 | CO2CH3 | CH3 | H |
| 179 | H | 2-pyrimidinyl-N(piperazine)-2-CH2O(CH2)4N | NO2 | CH3 | CO2CH3 | CH3 | H |
| 180 | H | 2-OCH3-C6H4-N(piperazine)-3-CH2O(CH2)4N | NO2 | CH3 | CO2CH3 | CH3 | H |
| 181 | H | 2-OCH3-C6H4-N(piperazine)-3-CH2O(CH2)4N | CN | CH3 | CO2CH3 | CH3 | H |
| 182 | 3-NO2 | 2-OCH3-C6H4-N(piperazine)-2-CH2O(CH2)3N | NO2 | CH3 | CO2CH3 | CH3 | H |

TABLE 2-continued

| # | | | | | | |
|---|---|---|---|---|---|---|
| 183 | 3-F | 2-CH₂O(CH₂)₄N-[piperidine]-(2-CH₃O-phenyl) | NO₂ | CH₃ | CO₂CH₃ | H |
| 184 | H | 2-CH₂O(CH₂)₂N-[piperidine]-(2-CH₃O-phenyl) | -C(=O)-O-CH(CH₃)- (cyclic) | | CO₂CH₃ | H |
| 185 | 3-NO₂ | 2-CH₂O(CH₂)₃N-[piperidine]-(2-pyrimidinyl) | -C(=O)-O-CH(CH₃)- (cyclic) | | CO₂CH₃ | H |
| 186 | 3-F | 2-CH₂O(CH₂)₃N-[piperidine]-(2-CH₃O-phenyl) | CONH₂ | CH₃ | CO₂CH₃ | H |
| 187 | H | 3-CH₂O(CH₂)₄N-[piperidine]-(2-pyrimidinyl) | CONH₂ | CH₃ | CO₂CH₃ | H |
| 188 | H | 2-O(CH₂)₃N-[piperidine]-(2-CH₃O-phenyl) | -C(=O)-O-CH(CH₃)- (cyclic) | | CO₂CH₃ | H |
| 189 | H | 2-O(CH₂)₄N-[piperidine]-(2-CH₃O-phenyl) | -C(=O)-O-CH(CH₃)- (cyclic) | | CO₂CH₃ | |

TABLE 2-continued

| | | | | | | |
|---|---|---|---|---|---|---|
| 190 | H | 2-O(CH₂)₅N, CH₃O-phenyl-piperidine | O-CO- | CO₂CH₃ | CH₃ | H |
| 191 | H | 2-O(CH₂)₆N, CH₃O-phenyl-piperidine | O-CO- | CO₂CH₃ | CH₃ | H |
| 192 | H | 2-O(CH₂)₄N, pyrimidine-piperidine | O-CO- | CO₂CH₃ | CH₃ | H |
| 193 | H | 2-O(CH₂)₅N, pyridine-piperidine | O-CO- | CO₂CH₃ | CH₃ | H |
| 194 | H | 2-O(CH₂)₄N, CH₃O-phenyl-piperidine | O-CO- | CO₂Et | CH₃ | H |
| 195 | H | 2-O(CH₂)₆N, pyrimidine-piperidine | O-CO- | CO₂CH₃ | CH₃ | H |
| 196 | H | 3-O(CH₂)₂N, CH₃O-phenyl-piperidine | O-CO- | CO₂CH₃ | CH₃ | H (glassy[oo] solid) |

TABLE 2-continued

| | | | | | |
|---|---|---|---|---|---|
| 197 | H | 3-O(CH$_2$)$_6$N-piperazine-(2-OCH$_3$-phenyl) | ester-CH$_2$ | CO$_2$CH$_3$ | CH$_3$ | H |
| 198 | H | 3-O(CH$_2$)$_3$N-piperazine-(pyrimidin-2-yl) | ester-CH$_2$ | CO$_2$CH$_3$ | CH$_3$ | H |
| 199 | H | 3-O(CH$_2$)$_5$N-piperazine-(pyrimidin-2-yl) | ester-CH$_2$ | CO$_2$CH$_3$ | CH$_3$ | H |
| 200 | H | 3-O(CH$_2$)$_4$N-piperazine-(pyridin-2-yl) | ester-CH$_2$ | CO$_2$CH$_3$ | CH$_3$ | H |
| 201 | 3-CF$_3$ | 2-O(CH$_2$)$_4$N-piperazine-(2-OCH$_3$-phenyl) | ester-CH$_2$ | CO$_2$CH$_3$ | CH$_3$ | 6-CH$_3$ |
| 202 | 3-Cl | 2-O(CH$_2$)$_4$N-piperazine-(2-OCH$_3$-phenyl) | ester-CH$_2$ | CO$_2$CH$_3$ | CH$_3$ | H |
| 203 | 2-NO$_2$ | 3-O(CH$_2$)$_5$N-piperazine-(pyrimidin-2-yl) | ester-CH$_2$ | CO$_2$CH$_3$ | CH$_3$ | 5-NO$_2$ |

TABLE 2-continued

| | | | | | |
|---|---|---|---|---|---|
| 204 | 3-NO₂ | CH₃O— ⟨piperidine-phenyl⟩ 2-O(CH₂)₅N | [lactone structure] | CO₂CH₃ | CH₃ | H |
| 205 | 3-F | ⟨piperidine-pyridine⟩ 2-O(CH₂)₄N | [lactone structure] | CO₂CH₃ | CH₃ | H |
| 206 | 3-Cl | CH₃O— ⟨piperidine-phenyl⟩ 2-O(CH₂)₄N | [lactone structure] | CO₂CH₃ | CH₃ | 5-Cl |

[a]NMR: (Acetone d₆)δ 2.36 (s, 3H); 2.54 (s, 3H); 2.68 (m, 4H); 2.78 (t, 2H); 3.03 (m, 4H); 3.65 (s, 3H); 3.82 (s, 3H); 4.10 (t, 2H); 5.40 (s, 1H); 6.75 (m, 1H); 6.89 (m, 6H); 7.15 (t, 1H); 8.54 (br s, 1H).
[b]NMR: (CDCl₃)δ 2.27 (s, 3H); 2.48 (s, 3H); 2.60–3.30 (m, 10H); 3.63 (s, 3H); 3.79 (s, 3H); 3.86 (s, 3H); 4.07–4.23 (m, 2H); 5.63 (s, 1H); 6.71–7.01 (m, 8H).
[c]Mass Spec: 551.4 (M + H)
[d]Mass Spec: 567 (M + H)
[e]NMR: (CDCl₃)δ: 1.75 (m, 4H); 2.35 (s, 3H); 2.49 (m, 2H); 2.51 (s, 3H); 2.70 (m, 4H); 3.15 (m, 4H); 3.68 (s, 3H); 3.88 (s, 3H); 3.99 (m, 2H); 5.41 (s, 1H); 6.75 (m, 1H); 6.90 (m, 7H); 7.17 (t, 1H).
[f]Mass Spec: 561.2746 (Calcd. 561.2713)
[g]Mass Spec: 595 (M + H)
[h]Mass Spec: m/e 580.99 (Calcd. 581.30 M + H)
[i]NMR: (CDCl₃)δ: 1.58 (m, 4H); 1.86 (t, 2H); 2.25 (s, 3H); 2.43 (m, 2H); 2.47 (s, 3H); 2.68 (m, 4H); 3.11 (m, 4H); 3.63 (s, 3H); 3.79 (s, 3H); 3.90 (m, 2H); 5.62 (s, 1H); 6.72 (t, 1H); 6.90 (m, 6H); 7.23 (s, 1H).
[j]Mass Spec: m/e 609.34 (Calcd. 609.33)
[k]Mass Spec: m/e 564.2999 (Calcd. 564.2948)
[l]Mass Spec: 578 (M⁺); 579 (M + H)
[m]Mass Spec: m/e 611.3107 (Calcd. 611.3107)
[n]Mass Spec: 522.27 (Calcd. 522.27 M + H)
[o]NMR: (CDCl₃)δ: 1.75 (t, 3H); 2.00 (m, 2H); 2.32 (s, 3H); 2.50 (s, 3H); 2.60 (m, 2H); 2.70 (m, 4H); 3.14 (m, 4H); 3.85 (s, 3H); 4.00 (t, 2H); 4.12 (q, 2H); 5.38 (s, 1H); 6.75 (m, 1H); 6.90 (m, 7H); 7.17 (t, 1H)
[p]Mass Spec: 549.38 (Calcd. 549.27 M + H)
[q]Mass Spec: 551.35 (Calcd. 551.28 M + H)
[r]Mass Spec: 633.26 (Calcd. 633.29 M + H)
[s]Mass Spec: 549.16 (Calcd. 549.27 M + H)
[t]Mass Spec: 547.29 (Calcd. 547.25 M + H)
[u]Mass Spec: 521.33 (Calcd. 521.28 M + H)
[v]Mass Spec: 541.24 (Calcd. 541.22 M + H)
[w]Mass Spec: 565.32 (Calcd. 565.30 M + H)
[x]Mass Spec: 537.28 (Calcd. 537.27 M + H)
[y]Mass Spec: 582.27 (Calcd. 582.26 M + H)
[z]Mass Spec: 596.31 (Calcd. 596.27 M + H)
[aa]NMR: (CDCl₃)δ: 2.03 (m, 2H); 2.31 (s, 3H); 2.55 (s, 3H); 2.70 (m, 6H); 3.10 (m, 4H); 3.61 (s, 3H); 3.85 (s, 3H); 3.92 (m, 2H); 5.18 (s, 1H); 6.90 (m, 5H); 7.45 (bs, 1H); 7.60 (m, 2H).
[bb]Mass Spec: 610.28 (Calcd. 610.29 M + H)
[cc]Mass Spec: 633.24 (Calcd. 633.22 M + H)

TABLE 2-continued

*dd*Mass Spec: 591.37 (Calcd. 591.32 M + H)
*ee*Mass Spec: 599.29 (Calcd. 599.26 M + H)
*ff*NMR: (CDCl₃)δ 1.35 (s, 9H); 1.72 (m, 4H); 2.25 (s, 3H); 2.46 (s, 3H); 2.50 (m, 2H); 2.68 (m, 4H); 3.10 (m, 4H); 3.90 (s, 3H); 5.45 (s, 1H); 6.90 (m, 8H); 7.30 (t, 1H).
*gg*Mass Spec: m/e 582.38 (M⁺ Calcd. for C₂₉H₃₅N₅O₈, 582.26)
*hh*Mass Spec: m/e 596.43 (M⁺ Calcd. for C₃₆H₃₇N₅O₈, 596.27)
*ii*Mass Spec: m/e 610.19 (M⁺ Calcd. for C₃₁H₃₉N₅O₈, 610.29)
*jj*NMR: (CDCl₃)δ: 2.30 (s, 3H); 2.47 (s, 3H); 2.69 (m, 4H); 2.85 (t, 2H); 3.60 (s, 3H); 3.86 (m, 4H); 4.12 (t, 2H); 5.64 (s, 1H); 6.50 (m, 2H); 6.84 (t, 2H); 7.13 (m, 1H); 7.27 (d, 1H); 8.32 (d, 2H). Mass Spec: m/e 495.17 (M⁺ Calcd. for C₂₅H₃₀N₆O₅, 495.23)
*kk*NMR: (Acetone d₆)δ: 1.65 (m, 4H); 1.85 (m, 2H); 2.32 (s, 3H); 2.51 (s, 3H); 2.48 (m, 6H); 3.54 (s, 3H); 3.81 (t, 4H); 3.97 (t, 2H); 6.53 (s, 1H); 6.86 (t, 1H); 6.90 (d, 1H); 7.09 (t, 1H); 7.22 (d, 1H); 8.29 (d, 2H); 8.86 (br, s, 1H). Mass Spec: m/e 537.34 (M⁺ Calcd. for C₂₈H₃₆N₆O₅, 537.26)
*ll*NMR: (CDCl₃)δ 1.92 (t, 2H); 2.11 (s, 3H); 2.56 (m, 6H); 2.59 (s, 3H); 3.82 (m, 4H); 3.95 (d, 2H); 5.43 (s, 1H); 6.51 (t, 1H); 6.73 (d, 1H); 6.81 (d, 2H); 7.01 (t, 1H); 7.24 (m, 2H); 7.56 (d, 2H); 8.30 (d, 2H); 9.03 (br s, 1H); 9.32 (br s, 1H).
*mm*NMR: (CDCl₃)δ 1.46 (m, 6H); 1.62 (m, 2H); 2.30 (s, 3H); 2.48 (s, 3H); 2.56 (m, 6H); 3.59 (s, 3H); 3.86 (m, 4H);3.93 (s, 2H); 5.62 (s, 1H); 6.49 (t, 1H); 6.81 (t, 2H); 7.11 (t, 1H); 7.28 (d, 2H); 8.32 (d, 2H).
*nn*NMR: (CDCl₃)δ: 1.97 (m, 2H); 2.10 (s, 3H); 2.34 (s, 3H); 2.60 (m, 6H); 3.11 (m, 4H); 3.58 (s, 3H); 3.86 (s, 3H); 4.02 (t, 2H); 4.57 (s, 1H); 6.23 (br s, 1H); 6.75-7.02 (m, 7H); 7.20 (t, 1H). Mass Spec: m/e 516.2736 (Calcd. for C₃₀H₃₆N₄O₄, 516.2736)
*oo*NMR: (Acetone d₆)δ: 1.87 (m, 4H); 2.38 (s, 3H); 2.70 (m, 6H); 3.51 (s, 3H); 3.60 (t, 2H); 3.91 (m, 4H); 4.73 (s, 2H); 5.17 (s, 1H); 6.53 (t, 1H); 6.83 (t, 2H); 7.16 (m, 2H); 8.30 (d, 2H); 8.72 (br s, 1H).
*pp*NMR: (CDCl₃)δ: 1.55 (m, 4H); 1.83 (m, 2H); 2.03 (m, 2H); 2.45 (t, 2H); 2.67 (m, 4H); 2.97 (t, 2H); 3.10 (m, 4H); 3.58 (s, 3H); 3.62 (t, 2H); 3.95 (t, 2H); 4.69 (ABq, 2H); 5.63 (s, 1H); 6.86 (m, 4H); 7.18 (m, 4H); 8.64 (br s, 1H). Mass Spec: m/e 624.14 (M⁺ Calcd. for C₃₃H₄₅N₅O₇, 624.34).
*qq*NMR: (CDCl₃)δ: 2.26 (s, 3H); 2.47 (s, 3H); 2.73 (m, 4H); 2.93 (m, 2H); 3.63 (s, 3H); 3.78 (s, 3H); 3.90 (m, 4H); 4.16 (t, 2H); 5.66 (s, 1H); 6.48 (t, 1H); 6.73 (d, 1H); 6.87 (m, 2H); 7.03 (br s, 1H); 8.31 (d, 2H). Mass Spec.: m/e 525.36 (M⁺ Calcd. for C₂₆H₃₂N₆O₆, 525.25).
*rr*NMR: (CDCl₃)δ: 1.74 (m, 4H); 2.34 (s, 3H); 2.46 (t, 2H); 2.66 (m, 4H); 3.09 (m, 4H); 3.56 (s, 3H); 3.85 (s, 3H); 3.94 (t, 2H); 4.55 (dd, 2H); 4.85 (s, 1H); 6.50-7.50 (m, 8H); 7.69 (br s, 1H).
*ss*NMR: (CDCl₃)δ: 1.73 (m, 4H); 2.03 (s, 3H); 2.33 (s, 3H); 2.47 (t, 2H); 2.67 (m, 4H); 3.11 (m, 4H); 3.57 (s, 3H); 3.86 (s, 3H); 3.97 (t, 2H); 4.57 (s, 1H); 6.30 (br s, 1H); 6.80 (m, 7H); 7.20 (t, 1H).
*tt*NMR: (CDCl₃)δ: 1.80 (m, 4H); 1.97 (s, 3H); 2.32 (s, 3H); 2.50 (t, 2H); 2.68 (s, 3H); 3.11 (m, 4H); 3.52 (s, 3H); 3.86 (s, 3H); 4.03 (t, 2H); 5.09 (s, 1H); 6.01 (br s, 1H); 6.81-7.27 (m, 8H).
*uu*NMR: (CDCl₃)δ: 1.70 (m, 4H); 2.00 (s, 3H); 2.31 (s, 3H); 2.50 (m, 6H); 3.58 (s, 3H); 3.82 (t, 4H); 3.97 (t, 2H); 4.56 (t, 1H); 6.48 (t, 1H); 6.80 (m, 4H); 7.19 (t, 1H); 8.30 (d, 2H).
*vv*NMR: (CDCl₃)δ: 1.97 (m, 2H); 2.10 (s, 3H); 2.53 (s, 3H); 2.58 (m, 6H); 3.56 (s, 3H); 3.84 (t, 4H); 4.04 (t, 2H); 4.57 (s, 1H); 6.30 (br s, 1H); 6.48 (t, 1H); 6.80 (m, 3H); 7.22 (t, 1H); 8.31 (d, 2H). Mass Spec: m/e 488.2502 (Calcd. for C₂₇H₃₂N₆O₃, 488.2536).

The compounds shown in Table 3 can be prepared by the procedures described in Method G, paths a and b.

TABLE 3

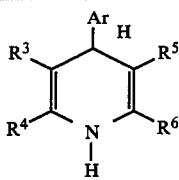

| Ex. No. | Ar | R³ | R⁴ | R⁵ | R⁶ |
|---|---|---|---|---|---|
| 207 | C₆H₅ | NO₂ | CH₃ | CO(CH₂)₃N-piperazinyl-(2-methoxyphenyl) 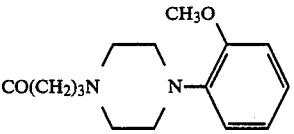 | CH₃ |
| 208 | 2-NO₂C₆H₄ | NO₂ | CH₃ | CO(CH₂)₃N-piperazinyl-(2-methoxyphenyl) 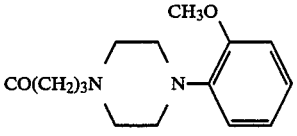 | CH₃ |
| 209 | 3-NO₂C₆H₄ | NO₂ | CH₃ | CO(CH₂)₃N-piperazinyl-(2-methoxyphenyl) 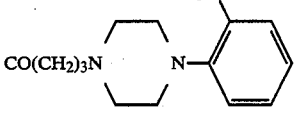 | CH₃ |
| 210 | 2-CF₃C₆H₄ | NO₂ | CH₃ | CH₂O(CH₂)₃N-piperazinyl-(2-methoxyphenyl) 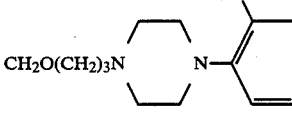 | CH₃ |
| 211 | 3-CF₃C₆H₄ | NO₂ | CH₃ | CH₂O(CH₂)₄N-piperazinyl-(2-methoxyphenyl) 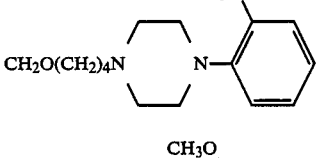 | CH₃ |
| 212 | 2-ClC₆H₄ | NO₂ | CH₃ | CO(CH₂)₄N-piperazinyl-(2-methoxyphenyl) 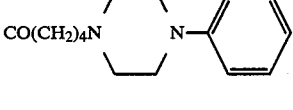 | CH₃ |
| 213 | 3-ClC₆H₄ | NO₂ | CH₃ | CH₂O(CH₂)₄N-piperazinyl-(2-methoxyphenyl) 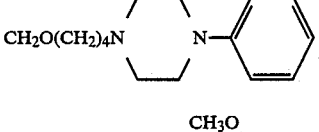 | CH₃ |
| 214 | 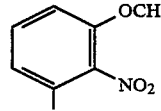 (2-OCH₃, 3-NO₂ phenyl) | NO₂ | CH₃ | CH₂O(CH₂)₂N-piperazinyl-(2-methoxyphenyl) 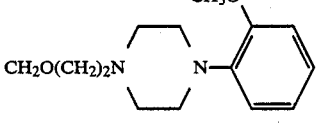 | CH₃ |
| 215 | 2-NO₂C₆H₄ | 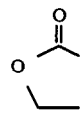 (ethoxycarbonyloxy) | | CO(CH₂)₃N-piperazinyl-(pyrimidinyl) 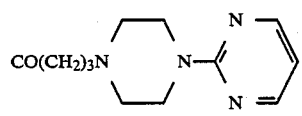 | CH₃ |

TABLE 3-continued

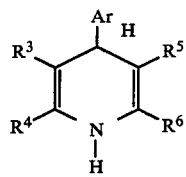

| Ex. No. | Ar | R³ | R⁴ | R⁵ | R⁶ |
|---|---|---|---|---|---|
| 216 | 2-CF₃C₆H₄ | —COOC₂H₅ | | CO(CH₂)₄N(piperazinyl)-2-pyridyl | CH₃ |
| 217 | 3-CF₃C₆H₄ | CN | CH₃ | CO(CH₂)₄N(piperazinyl)-2-pyridyl | CH₃ |
| 218 | 3-NO₂C₆H₄ | CN | CH₃ | CO(CH₂)₄N(piperazinyl)-(2-CH₃O-C₆H₄) | CH₃ |
| 219 | 2-ClC₆H₄ | CN | CH₃ | CO(CH₂)₄N(piperazinyl)-(2-CH₃O-C₆H₄) | CH₃ |
| 220 | 3-ClC₆H₄ | CONH₂ | CH₃ | CO(CH₂)₄N(piperazinyl)-(2-CH₃O-C₆H₄) | CH₃ |
| 221 | 2-NO₂C₆H₄ | CONH₂ | CH₃ | CO(CH₂)₄N(piperazinyl)-2-pyridyl | CH₃ |
| 222 | 3-NO₂C₆H₄ | CONH₂ | CH₃ | CO(CH₂)₄N(piperazinyl)-2-pyrimidinyl | CH₃ |

The compounds shown in Table 4 can be prepared as shown in Method G, path c.

TABLE 4

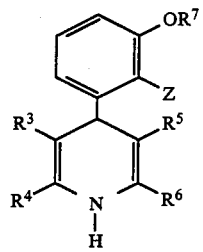

| Ex. No. | R³ | R⁴ | Z | R⁵ | R⁶ | R⁷ | mp° |
|---|---|---|---|---|---|---|---|
| 223 | NO₂ | CH₃ | −OC(=O)− | | CH₃ | (CH₂)₃N(piperazinyl)-2-methoxyphenyl | |
| 224 | NO₂ | CH₃ | −CH₂OC(=O)− | | CH₃ | (CH₂)₄N(piperazinyl)-2-methoxyphenyl | |
| 225 | NO₂ | CH₃ | −(CH₂)₃OC(=O)− | | CH₃ | (CH₂)₄N(piperazinyl)-2-methoxyphenyl | |
| 226 | NO₂ | CH₃ | −OC(=O)− | | CH₃ | (CH₂)₅N(piperazinyl)-2-methoxyphenyl | |
| 227 | CN | CH₃ | −OC(=O)− | | CH₃ | (CH₂)₄N(piperazinyl)-2-methoxyphenyl | |
| 228 | −C(=O)OCH₂CH₃ | | −OC(=O)− | | CH₃ | (CH₂)₅N(piperazinyl)-2-methoxyphenyl | |

Some examples of compounds wherein Ar is other than phenyl which can be prepared by the methods described in the specification are listed in Table 5.

TABLE 5

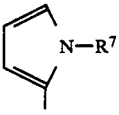

| Ex. No. | Ar | R³ | R⁴ | R⁵ | R⁶ | R⁷ | mp° |
|---|---|---|---|---|---|---|---|
| 229 | 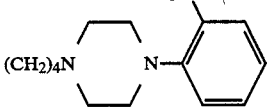 | NO₂ | CH₃ | CO₂CH₃ | CH₃ | (CH₂)₄N-piperazine-(2-methoxyphenyl) | |
| 230 | 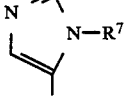 | NO₂ | CH₃ | CO₂CH₃ | CH₃ | (CH₂)₄N-piperazine-(2-methoxyphenyl) | |
| 231 | 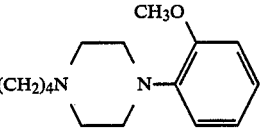 | NO₂ | CH₃ | CO₂CH₃ | CH₃ | (CH₂)₅N-piperazine-(2-pyrimidinyl) | |
| 232 | 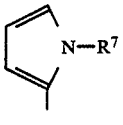 | NO₂ | CH₃ | CO₂CH₃ | CH₃ | (CH₂)₄N-piperazine-(2-methoxyphenyl) | |
| 233 | 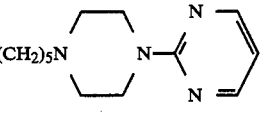 | NO₂ | CH₃ | CO₂CH₃ | CH₃ | (CH₂)₅N-piperazine-(2-methoxyphenyl) | |
| 234 | 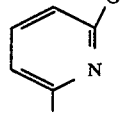 | CN | CH₃ | CO₂CH₃ | CH₃ | (CH₂)₃N-piperazine-(2-methoxyphenyl) | |
| 235 | 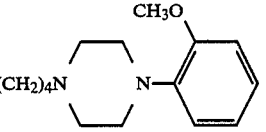 | CN | CH₃ | CO₂-iPr | CH₃ | (CH₂)₃N-piperazine-(2-methoxyphenyl) | |
| 236 | 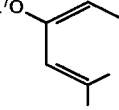 | CN | CH₃ | CO₂Et | CH₃ | (CH₂)₃N-piperazine-(2-methoxyphenyl) | |
| 237 | 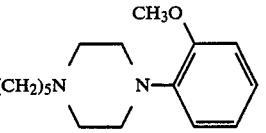 | CN | CH₃ | CO₂CH₃ | CH₃ | (CH₂)₃N-piperazine-(2-methoxyphenyl) | |

UTILITY

The compounds of this invention have been found to possess both $Ca^{2+}$ channel activity, preferably $Ca^{2+}$ agonist activity, and alpha₁-antagonist activity. These pharmacological properties of the compounds of this invention were evaluated in the following pharmacological experiments.

DETERMINATION OF AFFINITY FOR ALPHA$_1$-ADRENOCEPTORS

The [$^3$H]-prazosin binding assay was carried out according to the method described by Timmermans, P. B. M. W. M., Schoop, A. M. C., and Van Zwieten, P. A.: Biochem Pharmacol., 31, 899–905, 1982 (1). The reaction mixture contained partially purified rat brain membranes (source of alpha$_1$-adrenoceptors), 0.2 nM [$^3$H]-prazosin with or without potential displacer in Tris buffer. The mixture was incubated for 60 minutes at 25° and subsequently terminated by rapid filtration through glass fiber-filter. Receptor-bound [$^3$H]-prazosin trapped in the filter was quantitated by scintillation counting. The inhibitory concentration (IC$_{50}$) of potential displacer which gives 50% displacement of the total specifically bound [$^3$H]-prazosin is presented as a measure of the affinity of such compound for the alpha$_1$-adrenoceptor.

DETERMINATION OF AFFINITY FOR CALCIUM CHANNELS

[$^3$H]-Nitrendipine binding assay was carried out according to the method described by G. T. Bolger, et al., Biochem. Biophys. Res. Comm., 104, 1604–1609, 1982 (1). The reaction mixture contained rat cardiac microsomes (source of Ca$^{2+}$ channels), 0.5 nM [$^3$H]-nitrendipine with or without potential displacer in Tris buffer. The mixture was incubated for 60 minutes at 25° and subsequently terminated by rapid filtration through a glass fiber-filter. Membrane-bound [$^3$H]-nitrendipine trapped in the filter was quantitated by scintillation counting. The inhibitory concentration (IC$_{50}$) of potential displacer which gives 50% displacement of the total specifically bound [$^3$H]-nitrendipine is presented as a measure of the affinity of such compound for the Ca$^{2+}$ channel.

The results from the above two in vitro assays are summarized in Table 6.

TABLE 6

Binding Affinity Data for Calcium And alpha$_1$-adrenoceptor

| Example No. | [$^3$H]—Nitrendipine Binding IC$_{50}$ [M] | [$^3$H]—Prazosin Binding IC$_{50}$ [M] |
|---|---|---|
| 1 | $1.4 \times 10^{-7}$ | $9.6 \times 10^{-7}$ |
| 2 | $2.9 \times 10^{-8}$ | $8.0 \times 10^{-7}$ |
| 5 | $7.3 \times 10^{-8}$ | $4.9 \times 10^{-7}$ |
| 13 | $8.3 \times 10^{-7}$ | $>10^{-5}$ |
| 56 | $3.0 \times 10^{-7}$ | $3.0 \times 10^{-7}$ |
| 57 | $9.9 \times 10^{-7}$ | $9.7 \times 10^{-7}$ |
| 58 | $8.5 \times 10^{-7}$ | $1.3 \times 10^{-7}$ |
| 59 | $2.9 \times 10^{-7}$ | $1.3 \times 10^{-7}$ |
| 60 | $1.0 \times 10^{-6}$ | $4.9 \times 10^{-6}$ |
| 61 | $6.7 \times 10^{-8}$ | $1.1 \times 10^{-6}$ |
| 68 | $1.6 \times 10^{-5}$ | $5.9 \times 10^{-7}$ |
| 69 | $4.6 \times 10^{-6}$ | $3.5 \times 10^{-7}$ |
| 87 | $2.9 \times 10^{-6}$ | $4.8 \times 10^{-8}$ |
| 88 | $4.8 \times 10^{-6}$ | $2.6 \times 10^{-7}$ |
| 89 | $4.0 \times 10^{-6}$ | $7.1 \times 10^{-8}$ |
| 104 | $2.0 \times 10^{-7}$ | $8.6 \times 10^{-6}$ |
| 105 | $2.2 \times 10^{-7}$ | $1.8 \times 10^{-7}$ |
| 106 | $2.5 \times 10^{-7}$ | $1.4 \times 10^{-7}$ |
| 107 | $4.1 \times 10^{-6}$ | $4.1 \times 10^{-7}$ |
| 108 | $9.9 \times 10^{-7}$ | $1.2 \times 10^{-6}$ |
| 109 | $7.9 \times 10^{-7}$ | $6.1 \times 10^{-7}$ |
| 110 | $1.0 \times 10^{-6}$ | $1.6 \times 10^{-7}$ |
| 111 | $8.5 \times 10^{-7}$ | $1.9 \times 10^{-7}$ |
| 112 | $1.7 \times 10^{-6}$ | $1.8 \times 10^{-7}$ |
| 113 | $3.3 \times 10^{-6}$ | $5.7 \times 10^{-7}$ |
| 114 | $1.6 \times 10^{-6}$ | $2.4 \times 10^{-7}$ |
| 115 | $1.1 \times 10^{-4}$ | $1.3 \times 10^{-7}$ |
| 116 | $5.8 \times 10^{-7}$ | $5.0 \times 10^{-7}$ |
| 117 | $1.0 \times 10^{-5}$ | $2.8 \times 10^{-7}$ |
| 118 | $5.4 \times 10^{-7}$ | $8.5 \times 10^{-7}$ |
| 119 | $8.0 \times 10^{-7}$ | $4.9 \times 10^{-7}$ |
| 120 | $4.7 \times 10^{-7}$ | $4.4 \times 10^{-7}$ |
| 121 | $3.0 \times 10^{-6}$ | $8.2 \times 10^{-6}$ |
| 122 | $>10^{-5}$ | $2.3 \times 10^{-7}$ |
| 123 | $1.7 \times 10^{-6}$ | $4.5 \times 10^{-6}$ |
| 124 | $1.8 \times 10^{-5}$ | $1.2 \times 10^{-6}$ |
| 125 | $1.4 \times 10^{-6}$ | $4.4 \times 10^{-7}$ |
| 126 | $5.0 \times 10^{-6}$ | $2.9 \times 10^{-7}$ |
| 127 | $2.0 \times 10^{-6}$ | $2.7 \times 10^{-6}$ |
| 128 | $5.7 \times 10^{-6}$ | $1.0 \times 10^{-7}$ |
| 129 | $3.6 \times 10^{-7}$ | $3.8 \times 10^{-7}$ |
| 130 | $3.8 \times 10^{-7}$ | $3.3 \times 10^{-7}$ |
| 131 | $3.6 \times 10^{-6}$ | $1.5 \times 10^{-7}$ |
| 132 | $2.3 \times 10^{-6}$ | $1.3 \times 10^{-7}$ |
| 133 | $4.2 \times 10^{-7}$ | $7.5 \times 10^{-7}$ |
| 134 | $8.4 \times 10^{-6}$ | $3.4 \times 10^{-7}$ |
| 135 | $6.7 \times 10^{-6}$ | $4.3 \times 10^{-7}$ |
| 136 | $>10^{-5}$ | $>10^{-5}$ |
| 137 | $6.1 \times 10^{-6}$ | $4.4 \times 10^{-7}$ |
| 138 | $2.2 \times 10^{-7}$ | $2.8 \times 10^{-7}$ |
| 139 | $1.2 \times 10^{-7}$ | $1.4 \times 10^{-7}$ |
| 140 | $1.6 \times 10^{-7}$ | $1.8 \times 10^{-7}$ |
| 141 | $6.3 \times 10^{-7}$ | $8.3 \times 10^{-7}$ |
| 142 | $1.8 \times 10^{-7}$ | $2.5 \times 10^{-7}$ |
| 143 | $1.9 \times 10^{-7}$ | $3.5 \times 10^{-7}$ |
| 144 | $1.3 \times 10^{-6}$ | $3.1 \times 10^{-7}$ |
| 145 | $1.8 \times 10^{-7}$ | $6.3 \times 10^{-7}$ |
| 146 | $4.7 \times 10^{-7}$ | $9.9 \times 10^{-7}$ |
| 149 | $8.9 \times 10^{-6}$ | $2.9 \times 10^{-7}$ |
| 150 | $4.0 \times 10^{-6}$ | $2.2 \times 10^{-7}$ |
| 151 | $4.7 \times 10^{-6}$ | $2.0 \times 10^{-7}$ |
| 152 | $6.9 \times 10^{-7}$ | $2.7 \times 10^{-7}$ |
| 153 | $8.8 \times 10^{-7}$ | $1.2 \times 10^{-7}$ |
| 154 | $1.4 \times 10^{-6}$ | $9.3 \times 10^{-6}$ |
| 155 | $2.5 \times 10^{-7}$ | $2.6 \times 10^{-6}$ |

PROTOCOL FOR POSITIVE INOTROPIC EFFECT IN GUINEA PIG LEFT ATRIA

Guinea pigs are killed by cervical dislocation. The left atria are removed and mounted at 1 gm resting tension in tissue baths containing oxygenated Krebs bicarbonate solution which is kept at 37°. The left atria are electrically paced at 2Hz with square wave pulses of 1 msec duration. The voltage is set at 1.5× threshold level.

After a one hour equilibration period, control values for developed tension (DT, gm) are recorded. Test compounds are then added to the baths, in a cumulative manner to a maximum concentration of 10$^{-4}$, to obtain a concentration-response curve. Treatment values of DT are obtained after the rug effect has reached a plateau and the exposure time for each concentration is 5–8 minutes. Percent change of the treatment value from the control value is calculated at each concentration of the test compound. The results are shown in Table 7 below.

TABLE 7

| Ex. No. | EC$_{50}$(M)[a] | Intrinsic Activity[b] |
|---|---|---|
| Control-Bay K8644 | $1.5 \times 10^{-7}$ | 100 |
| 1 | $2.7 \times 10^{-5}$ | 30 |
| 2 | $4.4 \times 10^{-8}$ | 145 |
| 5 | $5.6 \times 10^{-7}$ | 100 |
| 13 | $3.0 \times 10^{-5}$ | 50 |

TABLE 7-continued

| Ex. No. | EC$_{50}$(M)$^a$ | Intrinsic Activity$^b$ |
|---|---|---|
| 56 | $6.0 \times 10^{-6}$ | 100 |
| 58 | $1.9 \times 10^{-6}$ | 90 |
| 59 | $1.0 \times 10^{-6}$ | 35 |
| 60 | $1.0 \times 10^{-6}$ | 50 |
| 61 | $>10^{-4}$ | 10 |
| 69 | $>10^{-4}$ | 10 |
| 87 | $>10^{-4}$ | 0 |
| 88 | $2.0 \times 10^{-6}$ | 50 |
| 89 | $2.0 \times 10^{-5}$ | 20 |
| 105 | $3 \times 10^{-6}$ | 20 |
| 106 | $>10^{-4}$ | 0 |
| 107 | $>10^{-4}$ | 0 |
| 108 | $>10^{-4}$ | 0 |
| 109 | $>10^{-4}$ | 0 |
| 110 | $>10^{-4}$ | 0 |
| 111 | $>10^{-4}$ | 0 |
| 112 | $>10^{-4}$ | 0 |
| 113 | $>10^{-4}$ | 0 |
| 114 | $>10^{-4}$ | 0 |
| 116 | $>10^{-4}$ | 0 |
| 117 | $>10^{-4}$ | 0 |
| 120 | $3.0 \times 10^{-5}$ | 50 |
| 123 | $>10^{-4}$ | 0 |
| 125 | $>10^{-4}$ | 0 |
| 129 | $2.0 \times 10^{-6}$ | 15 |
| 130 | $3.0 \times 10^{-6}$ | 25 |
| 139 | $>10^{-4}$ | 0 |
| 140 | $>10^{-4}$ | 0 |
| 142 | $>10^{-4}$ | 0 |

$^a$EC$_{50}$(M) = concentration that increases DT by 50% above the control DT.
$^b$Intrinsic Activity is a ratio of the maximum effect of the test compound to that of Bay K 8644 and expressed in percent.

The foregoing test results suggest that compounds of their invention have utility in the treatment of congestive heart failure.

DOSAGE FORMS

Compounds of this invention can be administered to treat said deficiencies by any means that produces contact of the active agent with the agent's site of action in the body of a mammal. The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending on the use and known factors such as the pharmacodynamic characteristics of the particular agent, and its mode and route of administration; age, health, and weight of the recipient; nature and extend of symptoms, kind of concurrent treatment, frequency of treatment, and the effect desired. For use in the treatment of said diseases, a daily dosage of active ingredient can be about 50 to 1000 mg.

Dosage forms (compositions) suitable for administration contain from about 1 milligram to about 100 milligrams of active ingredient per unit. In these pharmaceutical compositions the active ingredient will ordinarily be present in an amount of about 0.5-95% by weight based on the total weight of the composition.

The active ingredient can be administered orally in solid dosage forms, such as capsules, tablets, and powders, or in liquid dosage forms, such as elixirs, syrups, and suspensions or parenterally, in sterile liquid dosage forms. Alternatively it can be administered sublingually by tablets, gels, pastes, patches or lozenges.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl or propyl-paraben, and chlorobutanol.

Suitable pharmaceutical carriers are described in *Remington's Pharmaceutical Sciences*, A. Osol, a standard reference text in this field.

Useful pharmaceutical dosage forms for administration of the compounds of this invention can be illustrated as follows:

CAPSULES

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

SOFT GELATIN CAPSULES

A mixture of active ingredient in a digestable oil such as soybean oil, cottonseed oil or olive oil is prepared and injected by means of a positive displacement pump into gelatin to form soft gelatin capsules containing 100 milligrams of the active ingredient. The capsules are washed and dried.

TABLETS

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

INJECTABLE

A parenteral composition suitable for administration by injection is prepared by stirring 1.5% by weight of active ingredient in 10% by volume propylene glycol. The solution is made to volume with water for injection and sterilized.

SUSPENSION

An aqueous suspension is prepared for oral administration so that each 5 milliliters contain 100 milligrams of finely divided active ingredient, 100 milligrams of sodium benzoate, 1.0 grams of sorbitol solution, U.S.P., and 0.025 milliliters of vanillin.

What is claimed is:

1. Compounds having the formula:

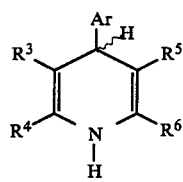

or a pharmaceutically acceptable salt thereof wherein Ar is

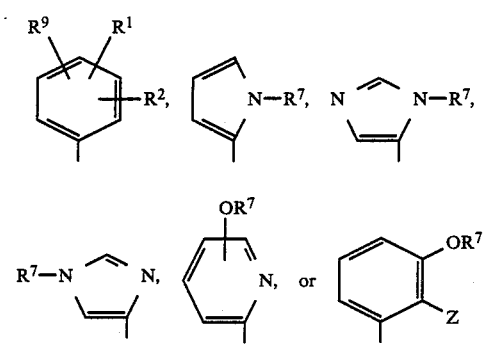

where Z and $R^5$ are taken together as

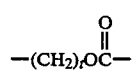

where t is 0 to 6;

$R^1$ and $R^2$ independently are H, alkyl of 1-4 carbon atoms, haloalkyl of 1-4 carbon atoms, haloalkoxy of 1-4 carbon atoms, alkoxy of 1-10 carbon atoms, halogen, $NO_2$, $(CH_2)_qXR^7$, $XCH_2(C_2-C_9$ alkenyl$)R^7$, or $XCH_2(C_2-C_9$ alkynyl$)R^7$; provided that both $R^1$ and $R^2$ are not hydrogen except when $R^5$ is $CO_2R^7$ or $COR^7$;

$R_3$ independently is $NO_2$, H, CN, or $CONH_2$, or taken together with $R^4$ is

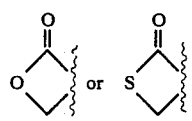

$R^4$ and $R^6$ independently are alkyl of 1-4 carbon atoms CN, $CH_2OH$, or $CH_2OCH_2CH_2NH_2$;

$R_5$ independently is $CO_2R^7$ or $COR^7$ when $R^1$ and $R^2$ are other than $(CH_2)_qXR^7$, $XCH_2(C_2-C_9$ alkenyl$)R^7$, or $XCH_2(C_2-C_9$ alkynyl$)R^7$, and can also be an alkyl ester of 1-10 carbon atoms,

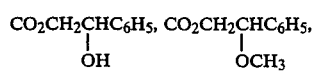

$NO_2$, or

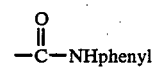

when one of $R^1$ or $R^2$ is $(CH_2)_qXR^7$, $XCH_2$ $(C_2-C_9$ alkenyl$)R^7$, or $XCH_2$ $(C_2-C_9$ alkynyl$)R^7$, or is taken together with Z as

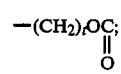

$R^7$ is selected from $-(A)_r-NH-Y-Ar'$, or

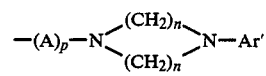

where A is a straight or branched alkyl, alkenyl or alkynyl chain;

Ar' is phenyl with one or two substituents selected from alkyl of 1-4 carbon atoms, haloalkyl of 1-4 carbon atoms, alkoxy of 1-4 carbon atoms, halogen, and $NO_2$; 2-, 3- or 4-pyridine; 2,6-pyrimidine;

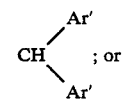

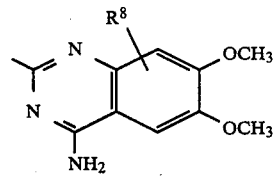

$R^8$ is H or $OCH_3$;
$R^9$ is H, halogen, $NO_2$, alkoxy of 1-4 carbon atoms, or alkyl of 1-4 carbon atoms;
X is O, S or NH;
Y is $(CH_2)_q$, $(CH_2)_nO$, $(CH_2)_nNH$ or $(CH_2)_nS$;
n is independently 1, 2 or 3;
p is 0 to 10;
q is 0, 1 or 2 and:
r is 1 to 10 provided that:
(1) when $R^5$ is $CO_2R^7$ and $R^7$ is

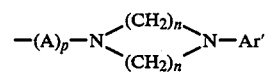

or where $R^2$ is $(CH_2)_qXR^7$, then p cannot be 0; and
(2) when $R^5$ is $COR^7$, then $R^7$ must be

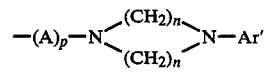

and p must be 0.

2. A compound of claim 1 wherein Ar is

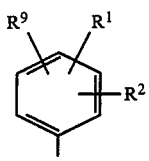

wherein $R^1$, $R^2$ and $R^9$ are as defined in claim 1.

3. A compound of claim 2 wherein one of $R^1$ and $R^2$ is hydrogen and the other is Cl, $CF_3$, $NO_2$, $OCH_3$ or $OR^7$, and $R^9$ is H or halogen.

4. A compound of claim 1 wherein $R^3$ independently is $NO_2$, or taken together with $R^4$ is

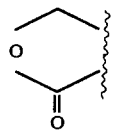

5. A compound of claim 1 wherein $R^4$ and $R^6$ independently are alkyl of 1–4 carbon atoms.

6. A compound of claim 1 wherein $R^5$ is $CO_2R^7$ or $COR^7$ and $R^1$ and $R^2$ are other than $(CH_{2q}XR^7$, $XCH_2(C_{2-C9}$ alkenyl)$R^7$ or $XCH_2(C_{2-C9}$ alkynyl)$R^7$.

7. A compound of claim 1 wherein $R^5$ is an alkyl ester of 1–10 carbon atoms, $NO_2$, or phenyl NHCO and one of $R^1$ or $R^2$ is $OR^7$.

8. A compound of claim 1 wherein $R^7$ is —$(CH_2)_r$—$NH(CH_2)_n$—O—Ar', or

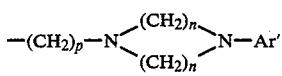

where Ar' is

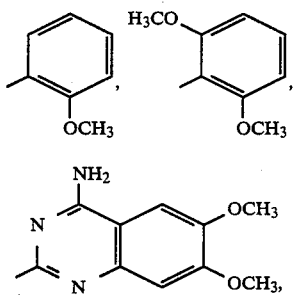

2-pyridine, or 2,6-pyrimidine.

9. A compound of claim 2 wherein $R^3$ independently is $NO_2$, or taken together with $R^4$ is

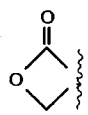

$R^4$ and $R^6$ independently are alkyl of 1–4 carbon atoms; and $R^5$ is an alkyl ester of 1–10 carbon atoms, $NO_2$, or phenyl NHCO; one of $R^1$ or $R^2$ is $OR^7$ and the other is H, Cl, $CF_3$, $NO_2$ or $OCH_3$; and $R^9$ is H or halogen.

10. A compound of claim 9 wherein $R^7$ is —$(CH_2)_r$—$NH(CH_2)_n$3 O—Ar', or

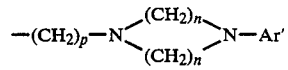

where Ar' is

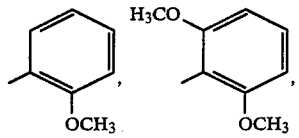

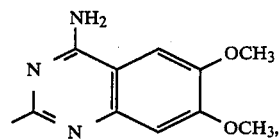

2-pyridine, or 2,6-pyrimidine.

11. A compound of claim 2 wherein one of $R^1$ and $R^2$ is H and the other is Cl, $CF_3$, $NO_2$, or $OCH_3$; $R^9$ is H or halogen; $R^3$ independently is $NO_2$, or taken together with $R^4$ is

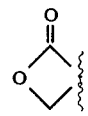

$R^4$ and $R^6$ independently are alkyl of 1–4 carbon atoms; and $R^5$ is $CO_2R^7$ or $COR^7$.

12. A compound of claim 11 wherein $R^7$ is —$(CH_2)_r$—$NH(CH_2)_n$—O—Ar', or

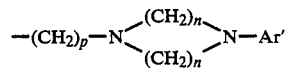

where Ar' is

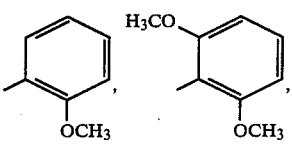

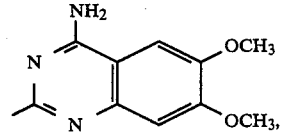

2-pyridine, or 2,6-pyrimidine.

13. A compound of claim 10 wherein $R^3$ is $NO_2$.
14. A compound of claim 12 wherein $R^3$ is $NO_2$.
15. A compound of claim 13 wherein $R^5$ is $CO_2CH_3$ or $NO_2$, and $R^7$ is

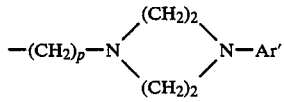

where Ar' is

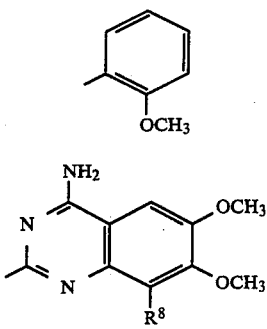

2-pyridine, or 2,6-pyrimidine.

16. A compound of claim 14 wherein R⁷ is

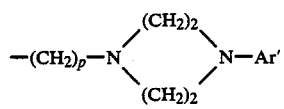

where Ar' is

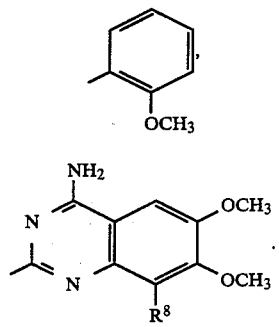

2-pyridine, or 2,6-pyrimidine.

17. The compound of claim 1 which is 1,4-Dihydro-2,6e dimethyl-5-nitro-4-[3-(trifluoromethyl)-1piperazinyl]-ethyl]ester-3-pyridinecarboxylic acid.

18. The compound of claim 1 which is 1,4-Dihydro-2,6dimethyl-4-[3-(2-((4(2-methoxyphenyl)-1-piperazinyl))ethoxy)-phenyl]-5-nitro-methyl ester-3-pyridinecarboxylic acid.

19. The compound of claim 1 which is 1,4-Dihydro-2,6-dimethyl-4-[2-(2-((4(2-methoxyphenyl)-1-piperazinyl))ethoxy)-phenyl]-5-nitro-methyl ester 3-pyridinecarboxylic acid.

20. The compound of claim 1 which is 1,4-Dihydro-2,6-dimethyl-4-[2-(2-((4-(2-methoxyphenyl)-1-piperazinyl))ethoxy)-3-(trifluoromethyl)phenyl]-5nitro-methylester-3-pyridinecarboxylic acid.

21. The compound of claim 1 which is 1,4-Dihydro-2,dimethyl-4-[2-(3-((4-(2-methoxyphenyl)-1-piperazinyl))propoxy)-phenyl]-5-methylester-3pyridinecarboxylic acid.

22. The compound of claim 1 which is 1–4-Dihydro-2,6dimethyl-5-nitro-4-[2-(4-(4-(2-pyrimidinyl)-piperazinyl)-butoxy)phenyl]-methylester-3pyridinecarboxlic acid.

23. The compound of claim 1 which is 1,4-Dihydro-2,dimethyl-4-[2-(5-(4-(2-methoxyphenyl)-1-piperazinyl)pentoxyl)-penyl]-5-nitro-methyl-ester-3-pyridinecarboxylic acid.

24. The compound of claim 1 which is 1,4-Dihydro-4-[2(10-(4-(2-methoxyphenyl)-piperazinyl)decyloxy)-phenyl]-5-nitro-methylester-3-pyridinecarboxylic acid.

25. A pharmaceutical composition for treating congestive heart failure consisting essentially of a pharmaceutically acceptable carrier and a therapeutically effective amount of a compound of claim 1.

26. A pharmaceutical composition consisting essentially of a pharmaceutically acceptable carrier and a therapeutically effective amount of a compound of claim 2.

27. A pharmaceutical composition consisting essentially of a pharmaceutically acceptable carrier and a therapeutically effective amount of a compound of aim 3.

28. A pharmaceutical composition consisting essentially of a pharmaceutically acceptable carrier and a therapeutically effective amount of a compound of claim 4.

29. A pharmaceutical composition consisting essentially of a pharmaceutically acceptable carrier and a therapeutically effective amount of a compound of claim 5.

30. A pharmaceutical composition consisting essentially of a pharmaceutically acceptable carrier and a therapeutically effective amount of a compound of claim 6.

31. A pharmaceutical composition consisting essentially of a pharmaceutically acceptable carrier and a therapeutically effective amount of a compound of claim 7.

32. A pharmaceutical composition consisting essentially of a pharmaceutically acceptable carrier and a therapeutically effective amount of a compound of claim 8.

33. A pharmaceutical composition consisting essentially of a pharmaceutically acceptable carrier and a therapeutically effective amount of a compound of claim 9.

34. A pharmaceutical composition consisting essentially of a pharmaceutically acceptable carrier and a therapeutically effective amount of a compound of claim 10.

35. A pharmaceutical composition consisting essentially of a pharmaceutically acceptable carrier and a therapeutically effective amount of a compound of claim 11.

36. A pharmaceutical composition consisting essentially of a pharmaceutically acceptable carrier and a therapeutically effective amount of a compound of claim 12.

37. A pharmaceutical composition consisting essentially of a pharmaceutically acceptable carrier and a therapeutically effective amount of a compound of claim 13.

38. A pharmaceutical composition consisting essentially of a pharmaceutically acceptable carrier and a therapeutically effective amount of a compound of claim 14.

39. A pharmaceutical composition consisting essentially of a pharmaceutically acceptable carrier and a therapeutically effective amount of a compound of claim 15.

40. A pharmaceutical composition consisting essentially of a pharmaceutically acceptable carrier and a therapeutically effective amount of a compound of claim 16.

41. A pharmaceutical composition consisting essentially of a pharmaceutically acceptable carrier and a therapeutically effective amount of the compound of claim 17.

42. A pharmaceutical composition consisting essentially of a pharmaceutically acceptable carrier and a therapeutically effective amount of the compound of claim 18.

43. A pharmaceutical composition consisting essentially of a pharmaceutically acceptable carrier and a therapeutically effective amount of the compound of claim 19.

44. A pharmaceutical composition consisting essentially of a pharmaceutically acceptable carrier and a therapeutically effective amount of the compound of claim 20.

45. A pharmaceutical composition consisting essentially of a pharmaceutically acceptable carrier and a therapeutically effective amount of the compound of claim 21.

46. A pharmaceutical composition consisting essentially of a pharmaceutically acceptable carrier and a therapeutically effective amount of the compound of claim 22.

47. A pharmaceutical composition consisting essentially of a pharmaceutically acceptable carrier and a therapeutically effective amount of the compound of claim 23.

48. A pharmaceutical composition consisting essentially of a pharmaceutically acceptable carrier and a therapeutically effective amount of the compound of claim 24.

49. A method for treating congestive heart failure in a mammal which comprises administering to the mammal a therapeutically effective amount of a compound of claim 1.

50. A method for treating congestive heart failure in a mammal which comprises administering to the mammal a therapeutically effective amount of a compound of claim 2.

51. A method for treating congestive heart failure in a mammal which comprises administering to the mammal a therapeutically effective amount of a compound of claim 3.

52. A method for treating congestive heart failure in a mammal which comprises administering to the mammal a therapeutically effective amount of a compound of claim 4.

53. A method for treating congestive heart failure in a mammal which comprises administering to the mammal a therapeutically effective amount of a compound of claim 5.

54. A method for treating congestive heart failure in a mammal which comprises administering to the mammal a therapeutically effective amount of a compound of claim 6.

55. A method for treating congestive heart failure in a mammal which comprises administering to the mammal a therapeutically effective amount of a compound of claim 7.

56. A method for treating congestive heart failure in a mammal which comprises administering to the mammal a therapeutically effective amount of a compound of claim 8.

57. A method for treating congestive heart failure in a mammal which comprises administering to the mammal a therapeutically effective amount of a compound of claim 9.

58. A method for treating congestive heart failure in a mammal which comprises administering to the mammal a therapeutically effective amount of a compound of claim 10.

59. A method for treating congestive heart failure in a mammal which comprises administering to the mammal a therapeutically effective amount of a compound of claim 11.

60. A method for treating congestive heart failure in a mammal which comprises administering to the mammal a therapeutically effective amount of a compound of claim 12.

61. A method for treating congestive heart failure in a mammal which comprises administering to the mammal a therapeutically effective amount of a compound of claim 13.

62. A method for treating congestive heart failure in a mammal which comprises administering to the mammal a therapeutically effective amount of a compound of claim 14.

63. A method for treating congestive heart failure in a mammal which comprises administering to the mammal a therapeutically effective amount of a compound of claim 15.

64. A method for treating congestive heart failure in a mammal which comprises administering to the mammal a therapeutically effective amount of a compound of claim 16.

65. A method for treating congestive heart failure in a mammal which comprises administering to the mammal a therapeutically effective amount of the compound of claim 17.

66. A method for treating congestive heart failure in a mammal which comprises administering to the mammal a therapeutically effective amount of the compound of claim 18.

67. A method for treating congestive heart failure in a mammal which comprises administering to the mammal a therapeutically effective amount of the compound of claim 19.

68. A method for treating congestive heart failure in a mammal which comprises administering to the mammal a therapeutically effective amount of the compound of claim 20.

69. A method for treating congestive heart failure in a mammal which comprises administering to the mammal a therapeutically effective amount of the compound of claim 21.

70. A method for treating congestive heart failure in a mammal which comprises administering to the mammal a therapeutically effective amount of the compound of claim 22.

71. A method for treating congestive heart failure in a mammal which comprises administering to the mammal a therapeutically effective amount of the compound of claim 23.

72. A method for treating congestive heart failure in a mammal which comprises administering to the mammal a therapeutically effective amount of the compound of claim 24.

* * * * *